(12) United States Patent
Palmer et al.

(10) Patent No.: US 8,337,424 B2
(45) Date of Patent: Dec. 25, 2012

(54) DEVICE FOR GUIDING OR EXCHANGING MEDICAL IMPLEMENTS AND MEDICAL EXCHANGE WIRE SYSTEM

(75) Inventors: Matthew Palmer, Miami, FL (US);
Kevin W. Smith, Coral Gables, FL (US);
Carlos Rivera, Cooper City, FL (US);
Derek Dee Deville, Miami, FL (US)

(73) Assignee: Syntheon, LLC, Miami, FL (US)

( * ) Notice: Subject to any disclaimer, the term of this patent is extended or adjusted under 35 U.S.C. 154(b) by 1715 days.

(21) Appl. No.: 11/637,329

(22) Filed: Dec. 12, 2006

(65) Prior Publication Data
US 2008/0108911 A1    May 8, 2008

Related U.S. Application Data

(60) Provisional application No. 60/856,573, filed on Nov. 3, 2006.

(51) Int. Cl.
*A61M 25/01* (2006.01)
*A61B 1/00* (2006.01)
*A61B 17/32* (2006.01)

(52) U.S. Cl. ........ 600/585; 600/104; 600/118; 600/131; 600/153; 600/434; 606/170; 606/159

(58) Field of Classification Search .................. 600/104, 600/115, 118, 131, 153–154, 434; 606/159, 606/170
See application file for complete search history.

(56) References Cited

U.S. PATENT DOCUMENTS

| | | | | |
|---|---|---|---|---|
| 5,782,748 | A * | 7/1998 | Palmer et al. | 600/104 |
| 7,156,528 | B2 * | 1/2007 | Weiss et al. | 359/529 |
| 7,789,825 | B2 * | 9/2010 | Nobis et al. | 600/131 |
| 2006/0264904 | A1 * | 11/2006 | Kerby et al. | 604/523 |

* cited by examiner

*Primary Examiner* — Ahmed Farah
*Assistant Examiner* — William Cheng
(74) *Attorney, Agent, or Firm* — Mayback & Hoffman, P.A.; Gregory L. Mayback; Thomas Bethea

(57) ABSTRACT

A medical guidewire system for guiding thereon a medical implement includes an end effector, an actuation guidewire having a distal end permanently connected to the end effector, and a control assembly. The assembly has a handle, a shaft receiving the guidewire. The shaft has a proximal end permanently connected to the handle and a distal end temporarily connected to the end effector. A first actuator is movably connected to the handle and operatively connected to the guidewire to actuate the end effector. A second actuator is movably connected to the handle and operatively connected to a portion of the guidewire to disconnect the guidewire from the handle when actuated and, thereby, permit removal of the control assembly from the end effector and guidewire. When the control assembly is removed, the end effector and the guidewire form a surgical exchange or guidewire for guiding thereon the medical implement.

20 Claims, 42 Drawing Sheets

DEVICE FOR GUIDING OR EXCHANGING MEDICAL IMPLEMENTS AND MEDICAL EXCHANGE WIRE SYSTEM

CROSS-REFERENCE TO RELATED APPLICATION

This application claims the priority, under 35 U.S.C. §119, of U.S. Provisional Patent Application No. 60/856,573 filed Nov. 3, 2006, the entire disclosure of which is hereby incorporated herein by reference in its entirety.

STATEMENT REGARDING FEDERALLY SPONSORED RESEARCH OR DEVELOPMENT n/a

FIELD OF THE INVENTION

The present invention lies in the field of endoscopic accessories and catheters, for example, devices that can be passed through the working channel of an endoscope (for example, a flexible endoscope) to manipulate tissue, a catheter sheath introducer in an intravascular procedure, and a trocar in a laparoscopic procedure. One possible catheter embodiment is a dissection device. An exemplary dissection device described in the present application is used, for example, to traverse a Chronic Total Occlusion (CTO). The present invention also relates to a medical exchange or guide wire system and device for guiding or exchanging a medical implement. One exemplary embodiment of the exchange wire system has a removable end effector-actuation wire assembly that can be separated from an actuation handle and the shaft surrounding the actuation wire. After use of the end effector in one medical process, the assembly can be decoupled from the handle and shaft to leave the actuation wire behind, which is, then, usable as a guidewire for another medical device for carrying out a subsequent surgical process.

BACKGROUND OF THE INVENTION

To gain access to treatment sites in the body, catheters must be flexible enough to conform to and follow natural anatomical pathways as they are advanced. These soft and delicate tissue pathways can be quite tortuous with many twists and turns. In the vasculature, this is especially the case, and even more so in certain areas of the vasculature such as the vessels of the brain and the coronary arteries.

When treating a site in the vasculature, the state-of-the-art practice is to first gain access to the treatment site with a flexible, steerable guidewire. Such a guidewire can be precisely controlled by the physician and steered into place using radiographic guidance. Once the guidewire is in-place, a device, referred to generally as a catheter, is advanced over the guidewire. The catheter must be flexible enough to smoothly follow the pathway of guidewire. After traversing the guidewire to the treatment site, the catheter can be used to deliver the treatment.

In the case of arterial blockage, the catheter may be a balloon dilatation catheter that is used to open the blockage. In such an embodiment, the guidewire is, first, passed up to and through the lesion. Then, the catheter is advanced over the guidewire and through the lesion. It is preferable to pass the guidewire through the blockage without aid of another device. However, if the guidewire is not able to penetrate the blockage, other aids are needed.

Currently, treatment of CTOs by catheter interventionalists is performed by attempting to pass the guidewire across the CTO. Once the guidewire is across, a low profile balloon catheter can be advanced over the guidewire to dilate the lesion. Such a procedure is almost always followed by placement of a stent. Specialty guidewires are available to aid the physician in this effort but they, too, are limited in their utility by the constraints of flexibility and compliance. It is noted that attempting to cross CTOs is a tedious practice with current equipment and is met with limited success.

In instances where the guidewire is not able to penetrate the blockage, different devices must be used successively to pass through the blockage and, then, effect the treatment. In one prior art procedure, the guidewire is advanced up to the blockage. Then, a micro-lumen catheter is advanced over the guidewire and against the blockage. A CTO penetrating device, such as the device sold by Cordis Corporation and referred to as the FRONTRUNNER® XP CTO, is threaded through the lumen of the micro-lumen catheter and up to the blockage. The penetrating device is actuated to penetrate through the blockage. When complete penetration is established, the micro-lumen catheter is advance over the penetrating device and through the blockage. The penetrating device is removed and the treatment catheter (e.g., balloon expanding or stent placing) is advanced through or around the micro-lumen catheter such that the treatment site surrounds the portion of the catheter used for treatment. If disposed within the micro-lumen catheter, it is removed before treatment is effected (i.e., before expansion of the balloon). A stent may or may not be deployed after the penetration of the blockage is widened.

It would be beneficial to provide a catheter, catheter system, and treatment process that can advance a device up to the treatment site with sufficient flexibility through a tortuous path, that can be used to penetrate a CTO, and that can also be used as an exchange wire for receiving thereover the treatment catheter to be used for opening the CTO for treatment with balloons or stents, for example.

SUMMARY OF THE INVENTION

The invention overcomes the above-noted and other deficiencies of the prior art by providing a catheter, a catheter system, a device for guiding or exchanging medical implements, a medical exchange wire system, and a treatment process that can advance a device up to the treatment site, penetrate a CTO, and be used as an exchange wire for receiving thereover the treatment catheter to be used for opening the CTO for treatment with balloons or stents.

Previously, many patients with CTOs did not have access to less-invasive procedures, like angioplasty or stenting, to open blockages. In order to treat CTOs with less-invasive methods, a doctor must first cross through the blockage. The present invention allows physicians to break through complete blockages and, thereby, allow treatment with stents or balloons. By using the catheter of the present invention, patients may avoid having to undergo difficult surgeries or even amputations.

With the foregoing and other objects in view, there is provided, in accordance with the invention, a medical guidewire system for guiding thereon a medical implement, including a surgical end effector for carrying out a medical procedure when actuated, an actuation guidewire having a distal end permanently connected to the end effector, and a control assembly. The control assembly has a handle, a hollow shaft receiving therein at least a portion of the actuation guidewire, a first actuator and a second actuator. The shaft has a proximal end permanently connected to the handle and a distal end temporarily connected to the end effector. The first actuator is movably connected to the handle and operatively connected to the actuation guidewire to actuate the end effector by the actuation guidewire through the shaft when the first actuator is actuated. The second actuator is movably connected to the handle and operatively connected to a portion of the actuation guidewire to disconnect the actuation guidewire from the handle when the second actuator is actuated and, thereby, permit removal of the control assembly from the end effector and the actuation guidewire and, when the control assembly is removed, the end effector and the actuation guidewire forming a surgical exchange wire or guidewire for guiding thereon the medical implement. As used herein, guidewire shall include both guidewires and exchanges wires and variations thereof.

With the objects of the invention in view, there is also provided a removable medical guidewire system, including a surgical end effector for carrying out a medical procedure when actuated, an actuation guidewire having a control connection portion and a distal end permanently connected to the end effector, and a control assembly. The control assembly has a handle, a hollow shaft receiving therein at least a portion of the actuation guidewire, an effector actuator, and a separation actuator. The shaft has a proximal end permanently connected to the handle and a distal end temporarily connected to the end effector. The effector actuator is movably connected to the handle for actuating the end effector and the separation actuator is movably connected to the handle for disconnecting the control assembly from the end effector and the actuation guidewire. The control connection portion has a guidewire connected state in which the control connection portion is operatively connected to the effector actuator to actuate the end effector in an actuation range when the effector actuator is actuated and a guidewire disconnected state in which the control connection portion is disconnected from the effector actuator by actuation of the separation actuator to permit removal of the control assembly from the end effector and the actuation guidewire, the end effector and the actuation guidewire together forming a surgical exchange wire or guidewire for guiding thereon a medical implement when the control assembly is removed.

With the objects of the invention in view, in a medical device having a handle with a shaft for receiving therein an actuation wire and an effector actuator movably connected to the handle for actuating an end effector, there is also provided an exchange wire or guidewire system including a surgical end effector temporarily connected to the effector actuator for carrying out a medical procedure when the effector actuator is actuated and temporarily connected to the shaft, an actuation guidewire having a distal end permanently connected to the end effector and being operatively connected between the effector actuator and the end effector through the shaft to actuate the end effector when the effector actuator is actuated, and a separation actuator movably connected to the handle and to a portion of the actuation guidewire, the separation actuator, when actuated, disconnecting the actuation guidewire from the effector actuator to permit removal of the handle from the end effector and the actuation guidewire and, when removed, the end effector and the actuation guidewire forming a surgical exchange wire or guidewire for guiding thereon a medical implement.

In accordance with another feature of the invention, the end effector and the shaft are sized to pass through a working channel of a flexible endoscope, a lumen of a catheter sheath introducer, and a lumen of a trocar to manipulate tissue. In one embodiment, the end effector is a dissection device shaped to traverse a Chronic Total Occlusion.

In accordance with a further feature of the invention, the shaft has an inner sheath surrounding a portion of the actuation guidewire, a coil surrounding the inner sheath, a sheath casing surrounding the coil, and a strain relief disposed at a junction of the handle and the coil and the sheath casing and surrounding the sheath casing.

In accordance with an added feature of the invention, the actuation guidewire moves inside the handle when the first actuator is actuated and the first actuator is a trigger assembly having an actuation coupler permanently connected to the actuation guidewire and movably disposed inside the handle to move in a corresponding manner with the actuation guidewire, a trigger body pivotally connected to the handle, and a trigger link having a first end pivotally connected to the trigger body and a second end pivotally connected to the actuation coupler, the trigger link moving the actuation coupler and, thereby, the actuation guidewire, when the trigger is actuated.

In accordance with an additional feature of the invention, the second actuator is connected to at least one of the actuation coupler and the actuation guidewire.

In accordance with yet another feature of the invention, the actuation coupler moves in an actuation range when the trigger body is actuated and the second actuator is connected to the actuation coupler and moves the actuation coupler outside the actuation range when actuated.

In accordance with yet a further feature of the invention, the handle has a boss; and the distal end of the actuation guidewire is a first end running from the end effector, through the shaft in a proximal direction, around the boss, back through the shaft in a distal direction, and terminating at a temporary connection on the end effector.

In accordance with yet an added feature of the invention, actuation of the first actuator moves the actuation guidewire in an actuation range insufficient to break the temporary connection and actuation of the second actuator moves the actuation outside the actuation range sufficient to break the temporary connection.

In accordance with yet an additional feature of the invention, the first actuator, when actuated, moves the actuation guidewire within an actuation range and the second actuator, when actuated, moves the actuation guidewire outside the actuation range to disconnect the actuation guidewire from the control assembly.

In accordance with again another feature of the invention, the second actuator, when actuated, moves at least portion of the actuation guidewire within the handle longitudinally further away from the end effector.

In accordance with again a further feature of the invention, the second actuator is a lever that, when pivoted, moves the actuation guidewire outside the actuation range.

In accordance with again an added feature of the invention, the second actuator is a screw that, when unscrewed, moves the actuation guidewire outside the actuation range.

In accordance with again an additional feature of the invention, the end effector has a frangible portion temporarily connecting the shaft to the end effector, the first actuator, when actuated, moves the actuation guidewire within an actuation range in which the frangible portion remains connected to the end effector, and the second actuator, when actuated, moves the actuation guidewire outside the actuation range to disconnect the actuation guidewire from the control assembly and disconnect the frangible portion from the end effector, thereby disconnecting the shaft from the end effector.

In accordance with still another feature of the invention, the frangible portion is fixed to the shaft when the second actuator is actuated and the frangible tube is disconnected from the end effector.

In accordance with a concomitant feature of the invention, the shaft has a coil surrounding at least a portion of the actuation guidewire and a sheath casing surrounding the coil, the end effector has a clevis with a proximal end, and the frangible portion is a fracture tube removably connected to the proximal end of the clevis and extending in a proximal direction therefrom into at least a portion of the coil and the sheath casing.

Other features that are considered as characteristic for the invention are set forth in the appended claims.

Although the invention is illustrated and described herein as embodied in a device for guiding or exchanging medical implements and medical exchange wire system, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

Advantages of embodiments of the present invention will be apparent from the following detailed description of the preferred embodiments thereof, which description should be considered in conjunction with the accompanying drawings in which.

DETAILED DESCRIPTION OF THE PREFERRED EMBODIMENTS

Figure 1:
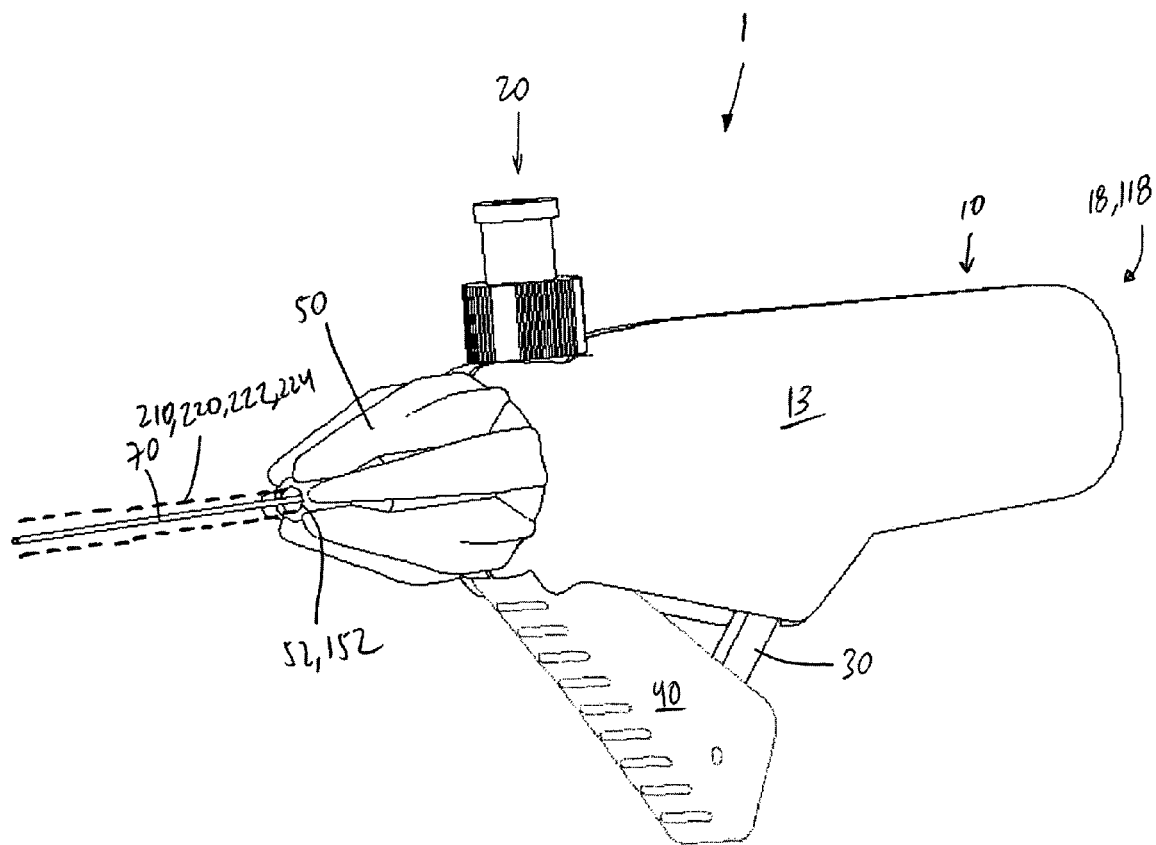
FIG. 1 is a fragmentary, perspective view of a device actuator according to an exemplary embodiment of the present invention from the side of a distal end thereof.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale. Further, it is noted that the figures have been created using a computer-aided design computer program. This program at times removes certain structural lines and/or surfaces when switching from a shaded or colored view to a wireframe view. Accordingly, the views should be considered as only illustrative.

Referring now to the figures of the drawings in detail and first, particularly to FIG. 1 thereof, there is shown a first exemplary embodiment of a medical device handle 1 according to the invention. The present application applies the medical device handle to a blunt dissection device for ease of understanding only. The invention is not limited to such dissection devices and can be applied to any medical device that has an end effector operated by a single actuation wire or an end effector operated by a single actuation wire and co-axially guided by an integrated guidewire.

Figure 2:
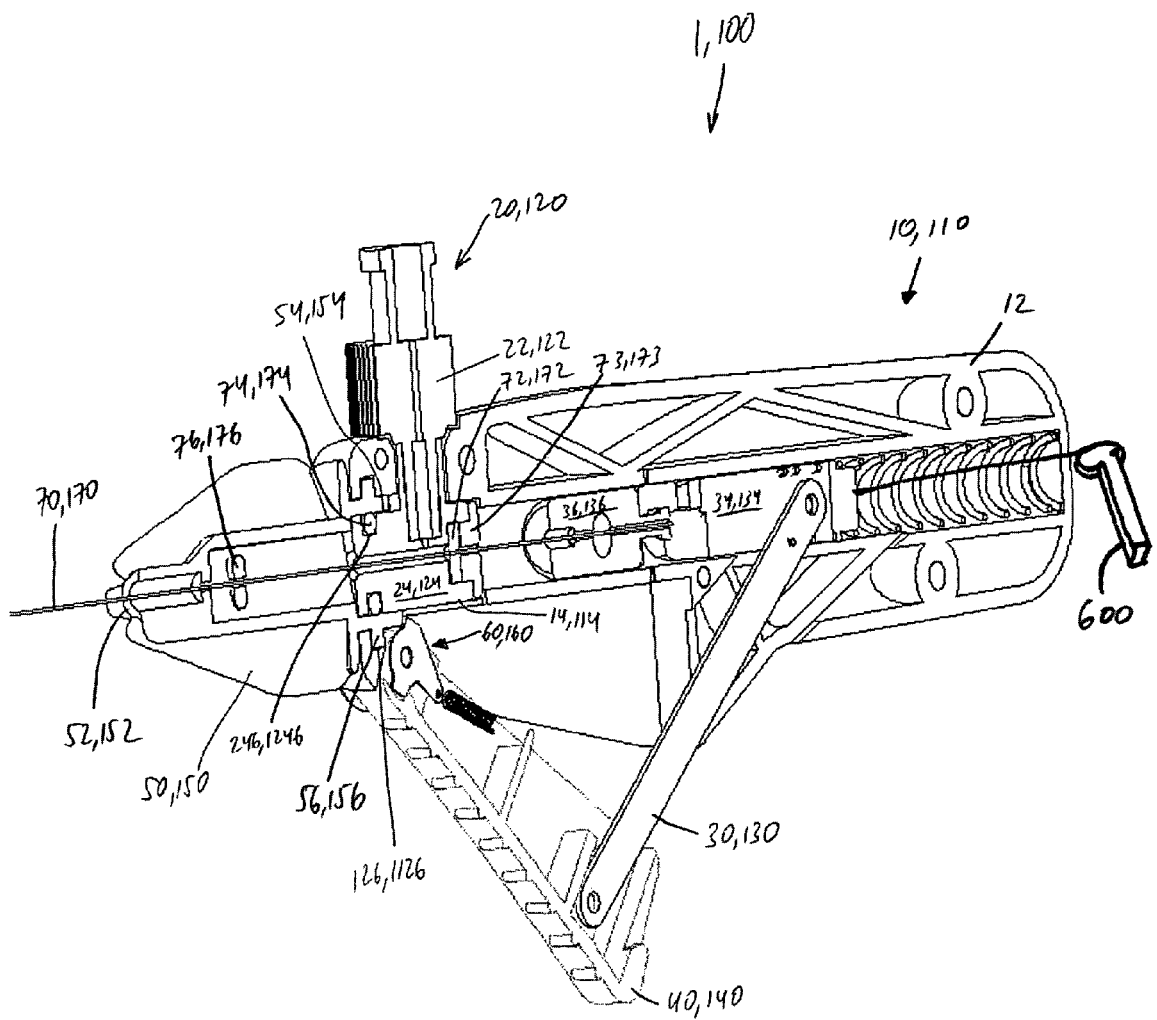
FIG. 2 is a fragmentary, perspective, longitudinally vertical cross-sectional view of the device actuator of FIG. 1.
Figure 3:
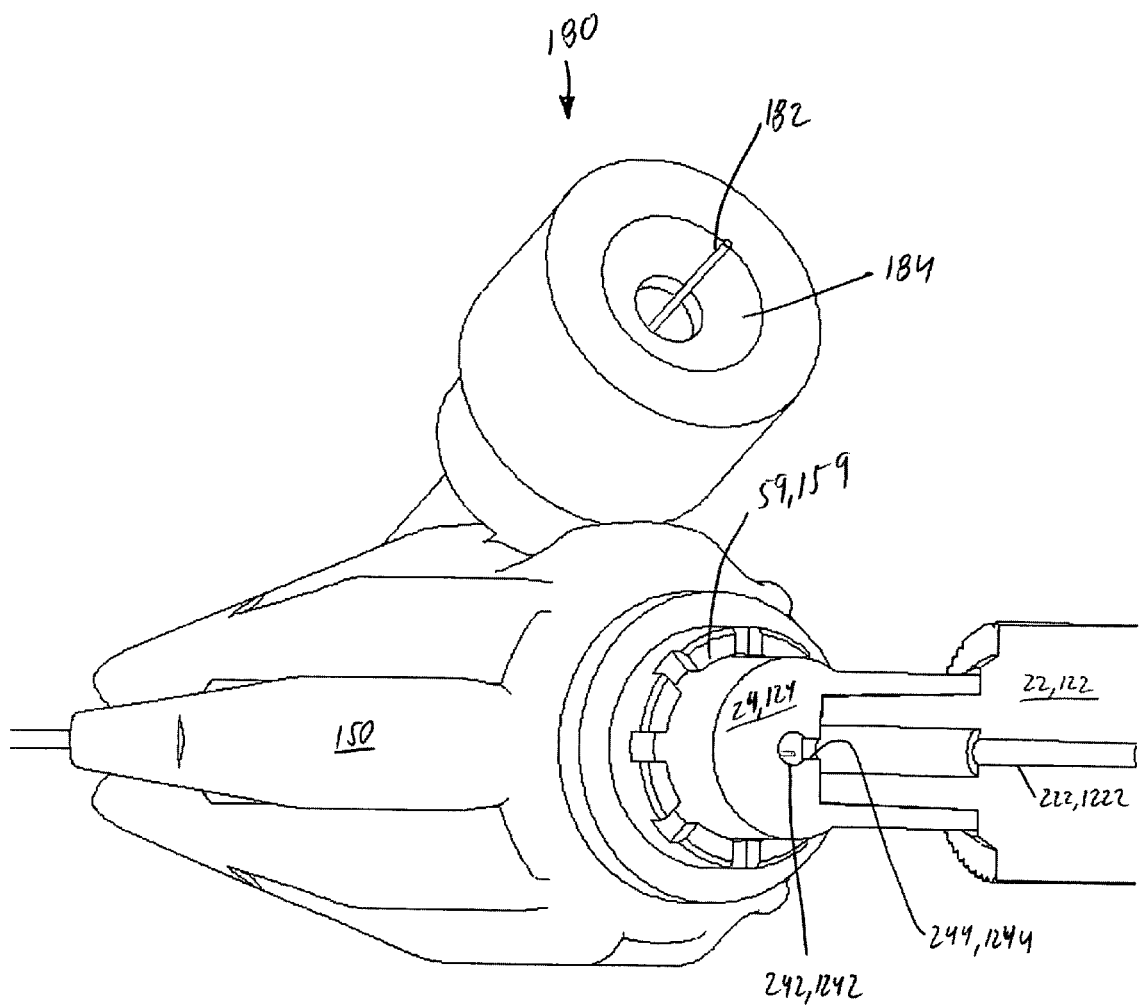
FIG. 3 is a fragmentary, perspective and partially transversely vertical cross-sectional view of a device actuator according to another exemplary embodiment of the present invention from the side of a proximal end thereof, shown with a side guidewire port.
Figure 4:
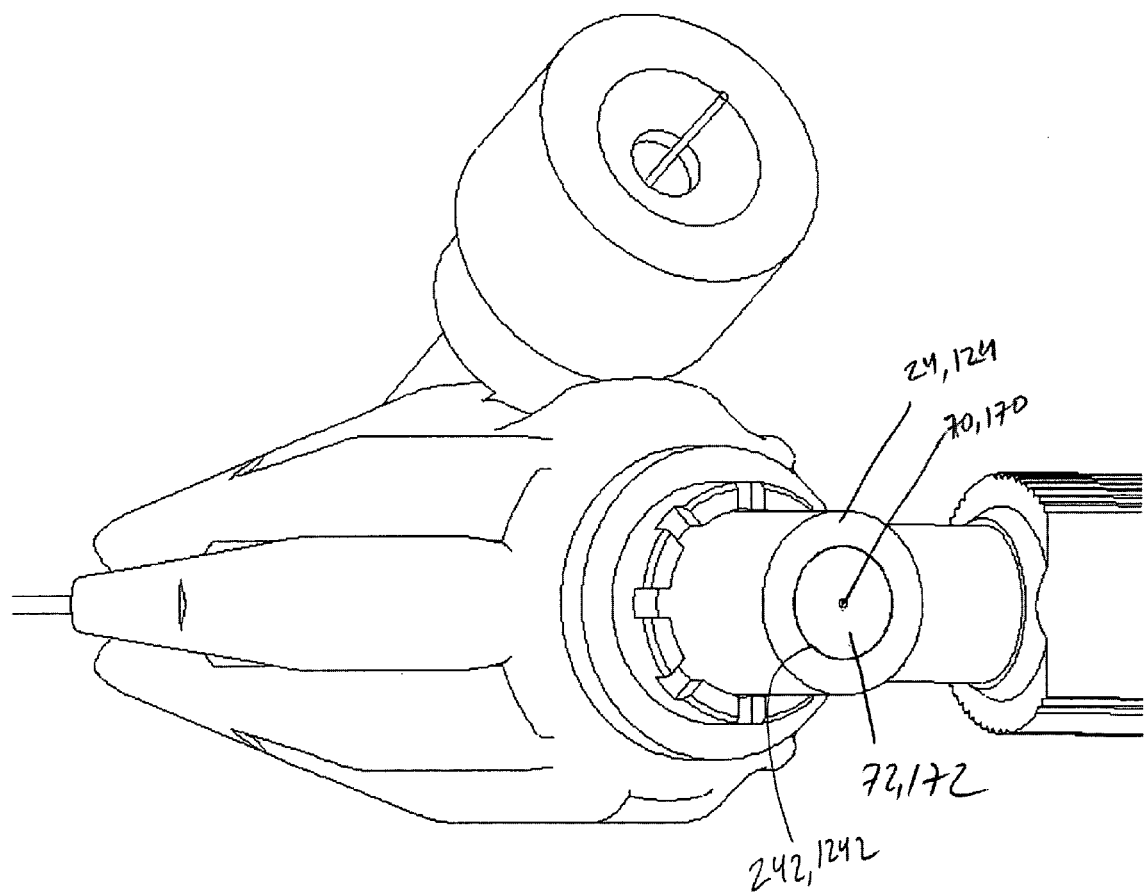
FIG. 4 is a fragmentary, perspective and partially transversely vertical cross-sectional view of the proximal portion of the device actuator of FIG. 3 in a further distal vertical plane therefrom.
Figure 5:
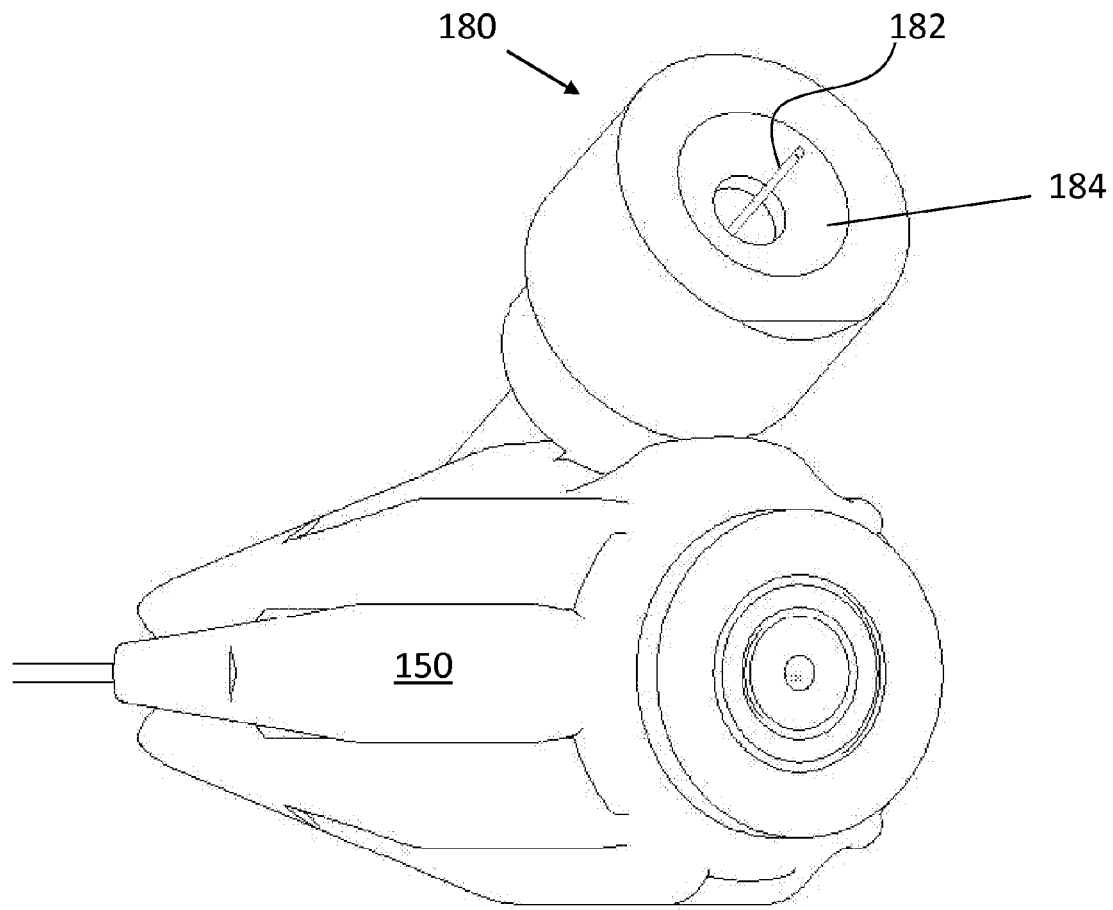
FIG. 5 is a fragmentary, perspective and partially transversely vertical cross-sectional view of the proximal portion of the device actuator of FIG. 4 in a further distal vertical plane therefrom.

The device handle 1 of FIGS. 1 to 2 includes a body casing 10, a purge valve 20, a trigger link 30, a trigger 40, a rotating distal nose 50, a nose lock-out assembly 60, and an actuation wire 70 (which is surrounded by a coil 220, an outer sheath 222, a strain relief portion 224, and, possibly, an inner sheath 210, the combination of which is only illustrated diagrammatically by dashed lines in FIG. 1). It is noted that a lubricious coating on the actuation wire 70, such as Teflon PTFE, can be used to perform the same function as the inner sheath 210. The coil can be made from, for example, stainless steel, and the sheath can be made from, for example, fluoropolymers, polyolefins (e.g., PTFE, HDPE, or FEP). The strain relief can be made from, for example, a heat-shrinkable material such as polyurethane or polyolefin.

In the exemplary embodiment of the body casing 10 shown, there are two halves 12, 13, the right half 12 only being illustrated in FIG. 2. The halves 12, 13 can be connected together in any manner, such as through solvent bonding, crush welding, and screws, to name a few.

An alternative configuration to the handle 1 of FIGS. 1 to 2 is the configuration shown in FIGS. 3 to 12 and 27 to 31. FIG. 2 can also be used with reference to this second configuration. This second handle 100 also has a body casing 110, a purge valve 120, a trigger link 130, a trigger 140, a rotating distal nose 150, a nose lock-out assembly 160, and an actuation wire 170.

The handle 100 further has an integral guidewire assembly 180. With such an assembly 180, a guidewire 182 can be inserted through a fluid-tight port 184 (e.g., a touhy-borst connector) in a portion of the handle 100 (without compromising the interior filled with saline, for example) and can exit from a distal end of the device 100 where an end effector 200, for example, is located. As will be described in detail below, the rotating nose 50, 150 is decoupled from the handle body 10, 110 and, therefore, the guidewire assembly 180 is connected to the nose 150 and not to the handle body 110.

The progression of FIGS. 3 to 11 illustrates a rotating distal nose 150 that includes this guidewire assembly 180. The cross-section of FIG. 2 illustrates the interior fluid passage of the purge valve 20, 120. The upstream portion 22, 122 of the valve 20, 120 extending transverse to the longitudinal axis of the casing 10, 110 can be a standard medical female luer fitting, as illustrated. The downstream portion—valve body 24, 124—is contained within a valve chamber 14, 114 of the body casing 10, 110. The valve body 24, 124 has a longitudinal fluid cavity 242, 1242 through which projects the actuation wire 170 and a transverse fluid cavity 244, 1244 fluidically connected to the longitudinal fluid cavity 242, 1242. It is noted that some of the figures of the drawings illustrate the actuation wire 70, 170 not centered at various portions of the handle. It is to be understood that the actuation wire 70, 170 is centrally disposed and aligned within the cavities of the handle and shaft and any figures illustrating an offset of the actuation wire should be deemed merely as an approximation of the device.

When the upstream portion 22, 122 of the purge valve 20, 120 is fluid-tightly connected to the valve body 24, 124, the fluid passage 222, 1222 is in fluidic communication with the transverse fluid cavity 244, 1244 (in this embodiment, the two passages 222, 1222 and 244, 1244 are coaxial). Therefore, when fluid (such as saline) is injected into the upstream port 224, 1224 of this configuration, it passes therethrough and, then, through the transverse fluid cavity 244, 1244 and the longitudinal fluid cavity 242, 1242, respectively. To prevent such fluid from passing anywhere proximal of the valve body 24, 124 (with respect to the longitudinal axis of the handle 1, 100):

- a seal disk 72, 172 is disposed at the proximal inside of the valve body 24, 124 and fluid tightly seals the space between the guidewire 70, 170 and walls of the longitudinal fluid cavity 242, 1242. The seal disk 72, 172 can be made of, for example, a silicone rubber disk that is held in place with a seal cap 73, 173; and
- an O-ring 74, 174 is disposed at the distal outside of the valve body 24, 124 and fluid tightly seals the space between the exterior surface of the valve body 24, 124 and the interior surface of a rear chamber of the nose 50, 150, which is rotatably disposed within the valve chamber 14, 114. The O-ring 74, 174 can be made of, for example, silicone rubber.

In this way, any injectate entering the upstream opening of the upstream portion 22, 122 travels out the distal opening 52, 152 of the nose 50, 150 and along the actuation wire 70, 170 (which is sealed within the coil 220 and the outer sheath 222 shown only diagrammatically with dashed lines in FIG. 1) until the fluid exits at the end effector 200.

FIG. 2 illustrates the interior of the device handle 1 with the left half 13 removed to permit view of the rotational and fluid-tight connection between the nose 50, 150 and the valve body 24, 124 and body casing 10, 110. The valve chamber 14, 114 is cylindrical. The O-ring 74, 174 is circular and, when installed within an O-ring groove 246, 1246, projects sufficiently far outside the groove 246, 1246 to fluid-tightly seal the interposed space between the outside of the valve body 24, 124 and the interior circular proximal chamber 54, 154 of the nose 50, 150, but not too far such that it presses the proximal end of the nose 50, 150 against the interior of the distal portion of the valve chamber 14, 114 that holds the nose 50, 150 therein. More specifically, the proximal end of the nose 50, 150 forms a circular tongue 56, 156 that fits, rotatably, within a circular-disc-shaped hollow groove 126, 1126 within the distal interior of the valve chamber 14, 114. Also provided on the proximal-most end of the nose 50, 150 is a castellated ring 59, 159, which is apparent in FIG. 3, for example. As will be discussed in detail below, the spaces between the castellations are used as a keyhole for receiving a locking tab 68, 168 that prevents the nose 50, 150 from rotating about its axis when the locking tab 68, 168 is positioned in one of the spaces between two castellations.

As will be described in further detail below, the end effector 200, the actuation wire 70, 170, the outer sheath 222 and the coil 220 surrounding the actuation wire 70, 170 are desired to turn together as one. When the sheath 222 and coil 220 are fastened to the nose 50, 150, for example, by bonding, these features will turn with the nose 50, 150 directly. The actuation wire 70, 170 and the inner sheath 210, however, are not coupled to either the nose 50, 150, the outer sheath 222, or the coil 220 because longitudinal uncoupling must be ensured to permit longitudinal movement of the actuation wire 70, 170 for end effector actuation.

Figure 6:
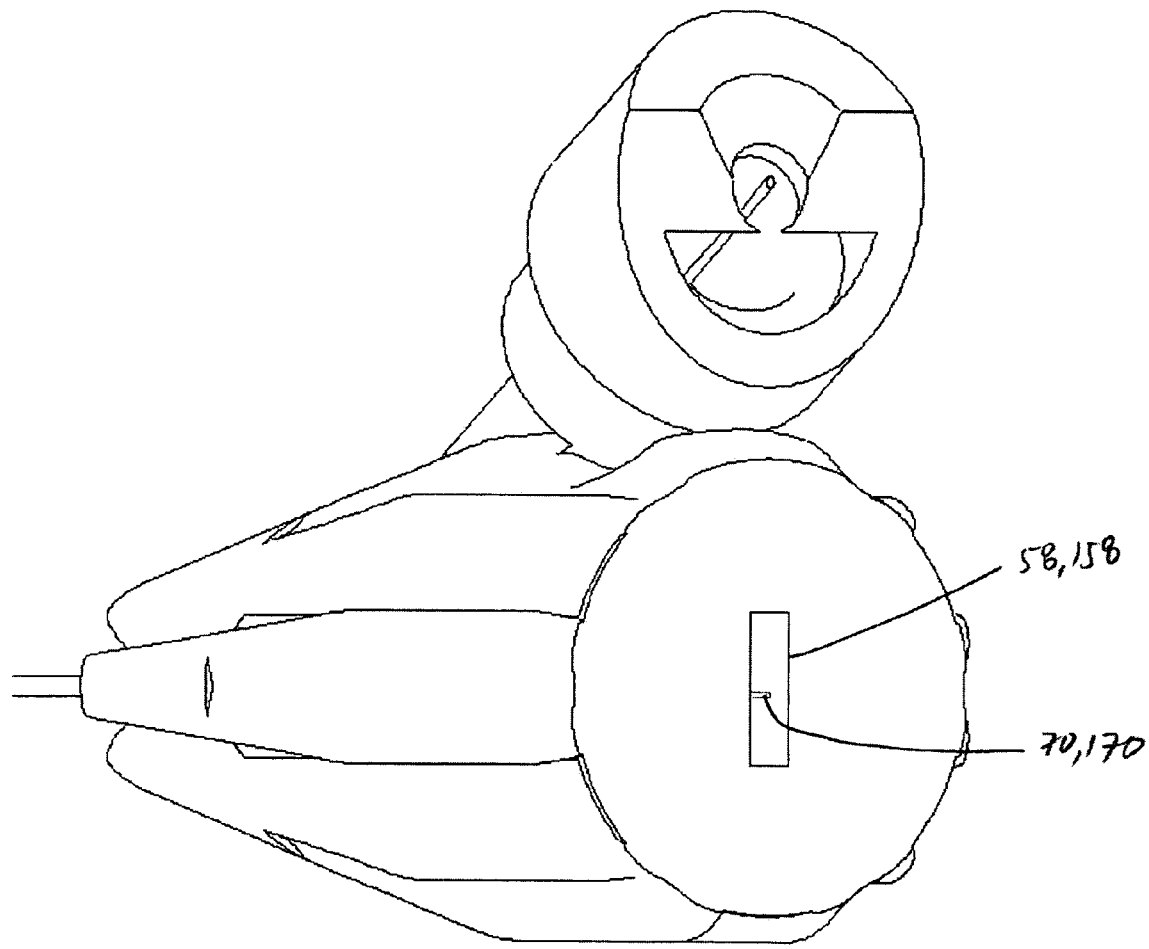
FIG. 6 is a fragmentary, perspective and partially transversely vertical cross-sectional view of the proximal portion of the device actuator of FIG. 5 in a further distal vertical plane therefrom.
Figure 7:
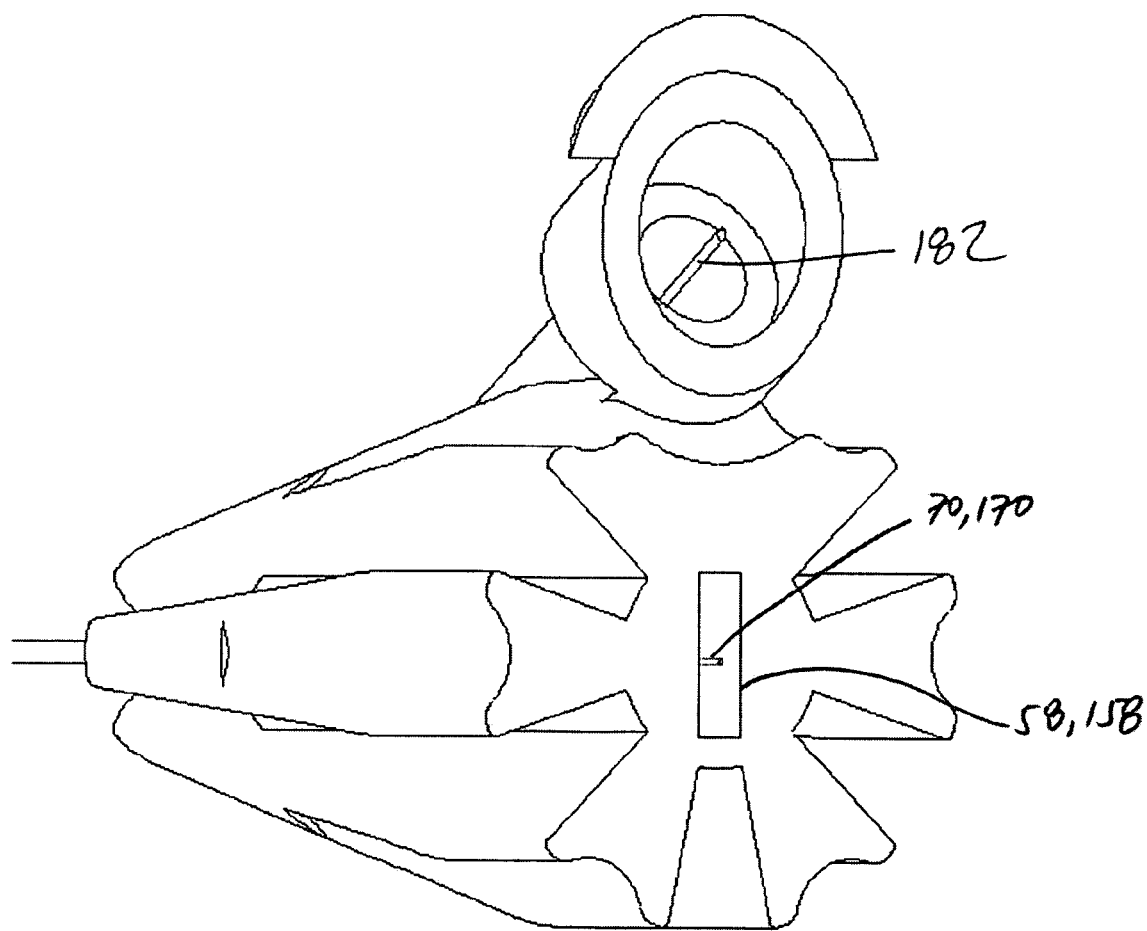
FIG. 7 is a fragmentary, perspective and partially transversely vertical cross-sectional view of the proximal portion of the device actuator of FIG. 6 in a further distal vertical plane therefrom.
Figure 8:
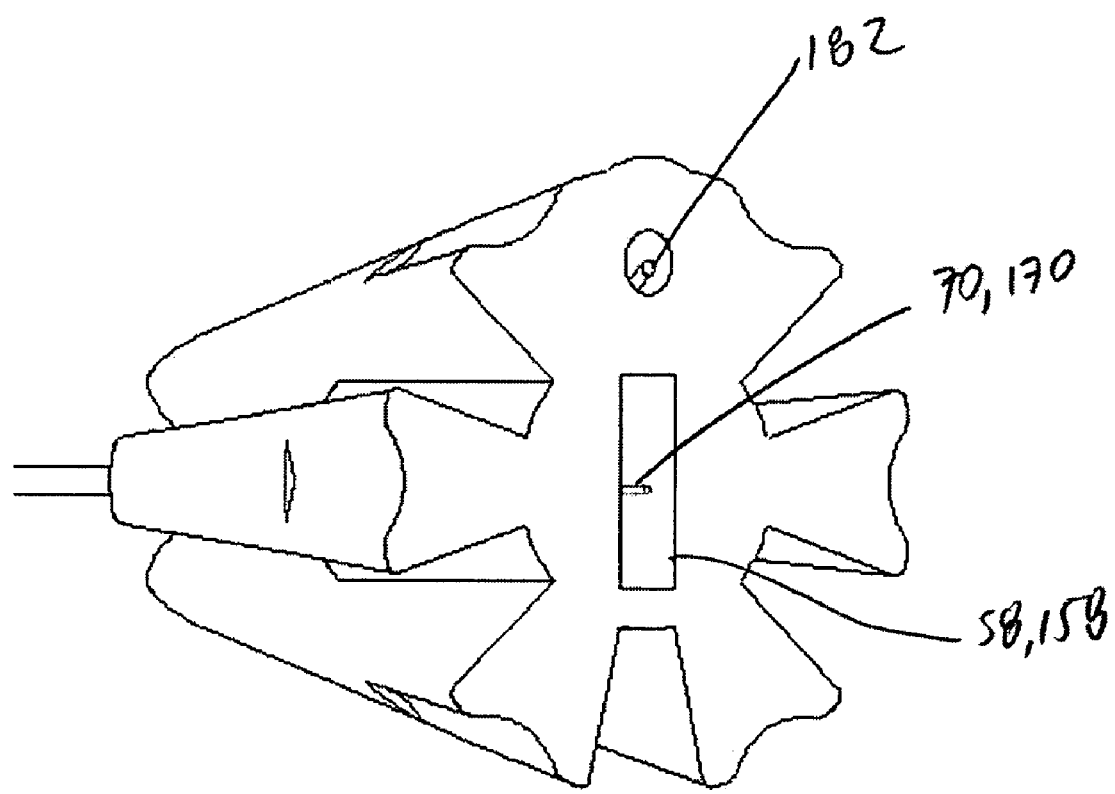
FIG. 8 is a fragmentary, perspective and partially transversely vertical cross-sectional view of the proximal portion of the device actuator of FIG. 7 in a further distal vertical plane therefrom.

To effect such a rotational coupling but provide the longitudinal uncoupling, a first embodiment of a torque couple is provided and is illustrated in FIG. 2 and, especially, in FIGS. 6 to 8. More specifically, a torque puck 76, 176 (see FIG. 14) is fastened to the actuation wire 70, 170 so that it rotates with the actuation wire 70, 170 and vice-versa—rotation of the puck 76, 176 causes rotation of the actuation wire 70, 170. In the exemplary embodiment, the puck 76, 176 has a rectangular cross-section. A torque groove 58, 158 within the nose 50, 150 has a corresponding shape but is slightly larger than the puck 76, 176 so that longitudinal movement of the puck 76, 176 within the groove 58, 58 is unhindered by the nose 50, 150. In such a configuration, when the nose 50, 150 is rotated with respect to the actuation wire 70, 170, the inside surfaces of the torque groove 58, 158 act against the puck 76, 176 to rotate the puck 76, 176 along with the nose 50, 150. An alternative embodiment of this connection is illustrated and described below with respect to FIGS. 18 to 19.

Figure 9:
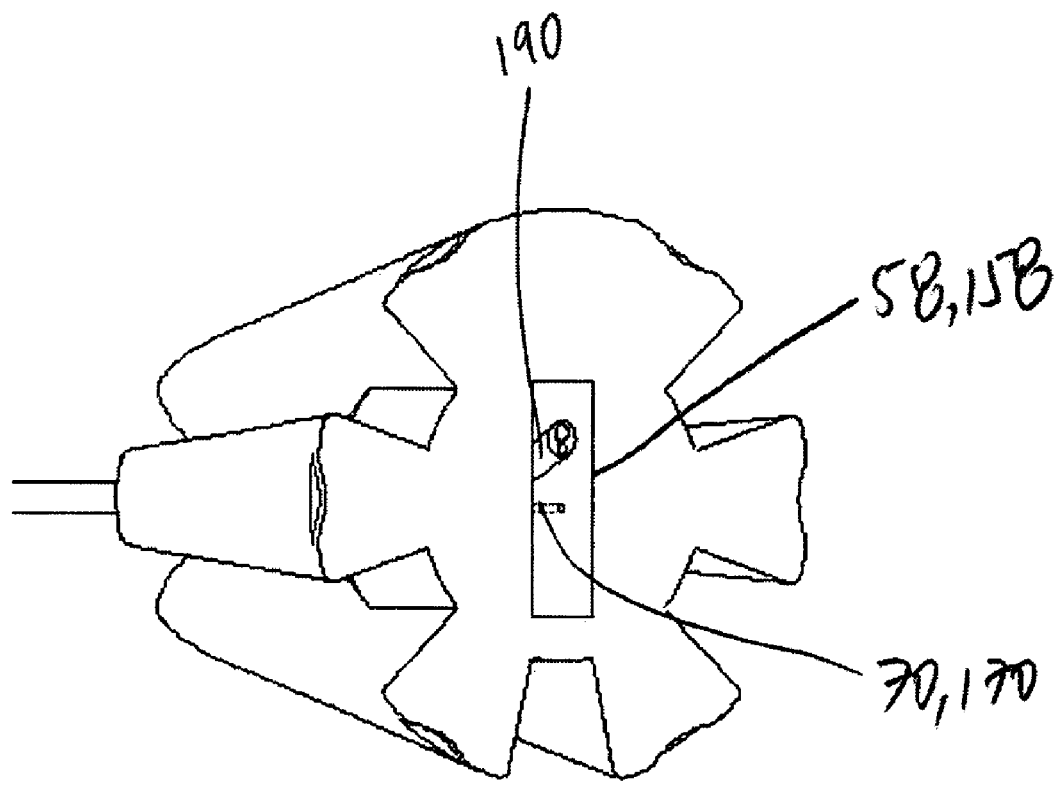
FIG. 9 is a fragmentary, perspective and partially transversely vertical cross-sectional view of the proximal portion of the device actuator of FIG. 8 in a further distal vertical plane therefrom.
Figure 10:
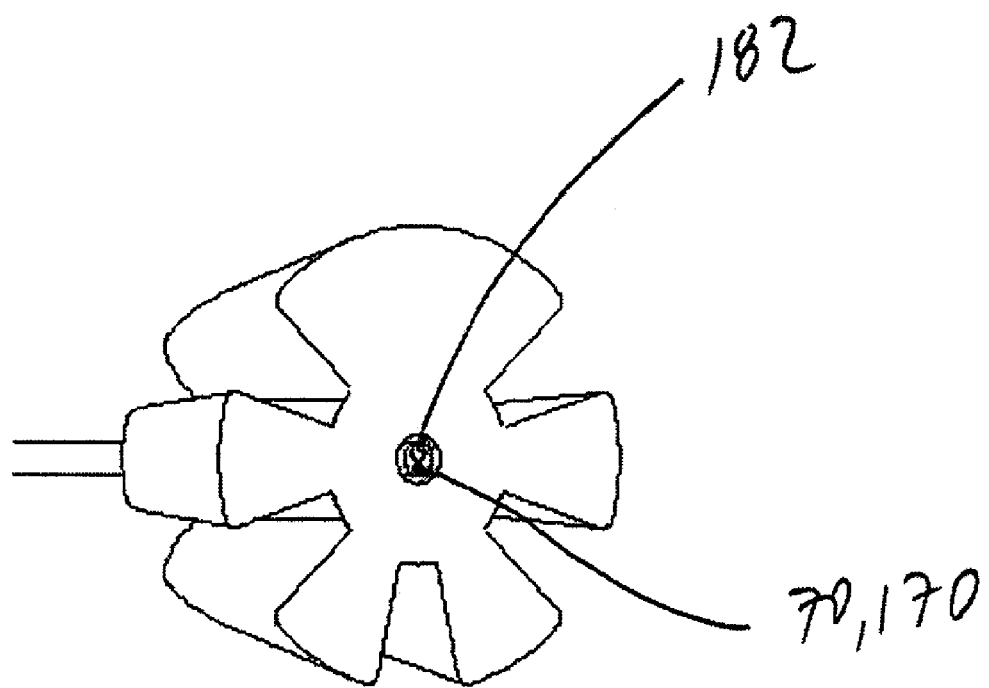
FIG. 10 is a fragmentary, perspective and partially transversely vertical cross-sectional view of the proximal portion of the device actuator of FIG. 9 in a further distal vertical plane therefrom.
Figure 11:
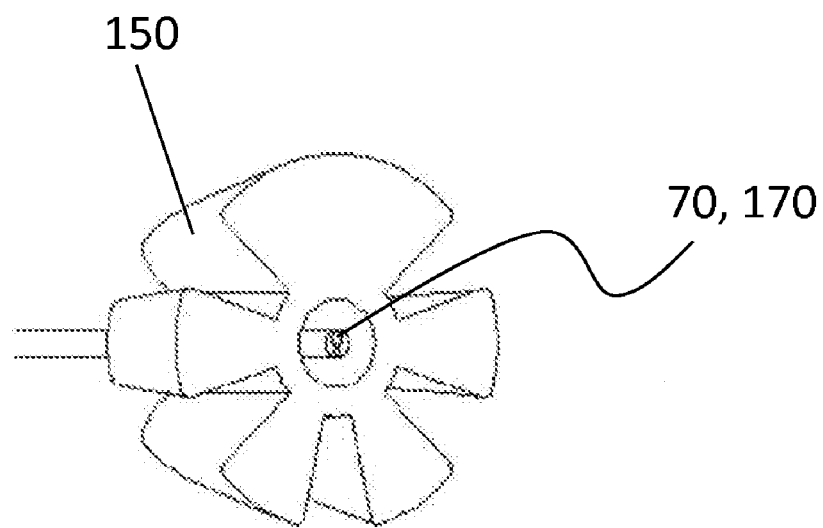
FIG. 11 is a fragmentary, perspective and partially transversely vertical cross-sectional view of the proximal portion of the device actuator of FIG. 10 in a further distal vertical plane therefrom.
Figure 12:
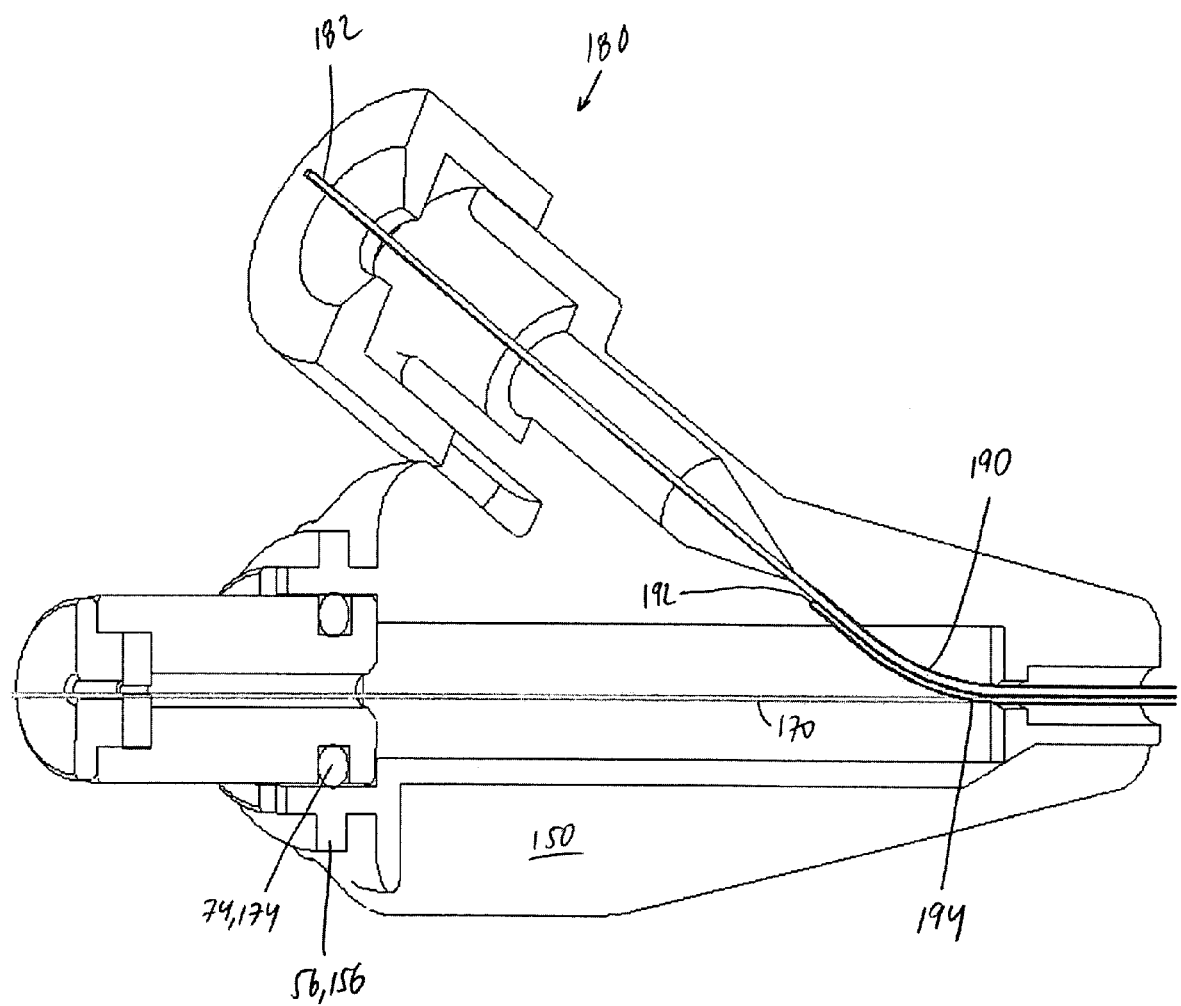
FIG. 12 is an enlarged, fragmentary, horizontally longitudinal cross-sectional view of the proximal portion of FIG. 3 with the guidewire port viewed from a bottom thereof.

FIG. 12 illustrates the separation of the guidewire 182 and the actuation wire 170 within the guidewire assembly 180 and the rotating nose 150. As can be seen in the progression of FIGS. 3 to 8, the guidewire 182 and the actuation wire 170 remain separate and traverse through separate passages at an angle to one another. FIGS. 10 to 11 show that these two wires 170, 182 become parallel and enter a two-lumen tube 190 before exiting the distal opening 152 of the nose 150. FIG. 9 clearly shows that the two-lumen tube 190 begins at a point at an angle to the actuation wire 70, 170 and FIG. 12 specifically illustrates the tube 190 extending along the guidewire 182 over a distance that does not include the actuation wire 170. There are various ways to permit the actuation wire 170 to enter the second of the two lumens at a point distal of the proximal opening 192. One such configuration creates a hole slightly larger than the actuation wire 170 at an entry point 194 shown in FIG. 12. Another such configuration cuts a groove between the second lumen and the outer circumference of the two-lumen tube 190 from the proximal opening 192 all the way to the entry point 194. The latter configuration is easier to manufacture because the portion of the second lumen that is peeled open can act as a guiding groove through which the actuation wire 170 can be threaded.

Figure 13:
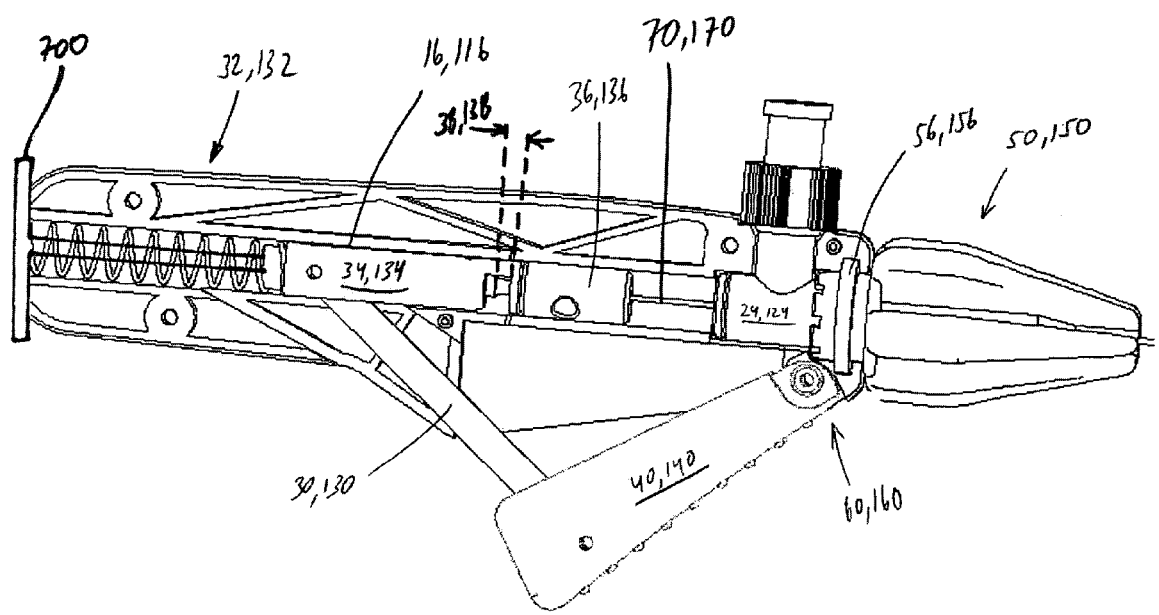
FIG. 13 is a fragmentary, partially longitudinally vertical cross-sectional view of the device actuator of FIG. 1 from a right side thereof with the actuation lever in the open position.
Figure 14:
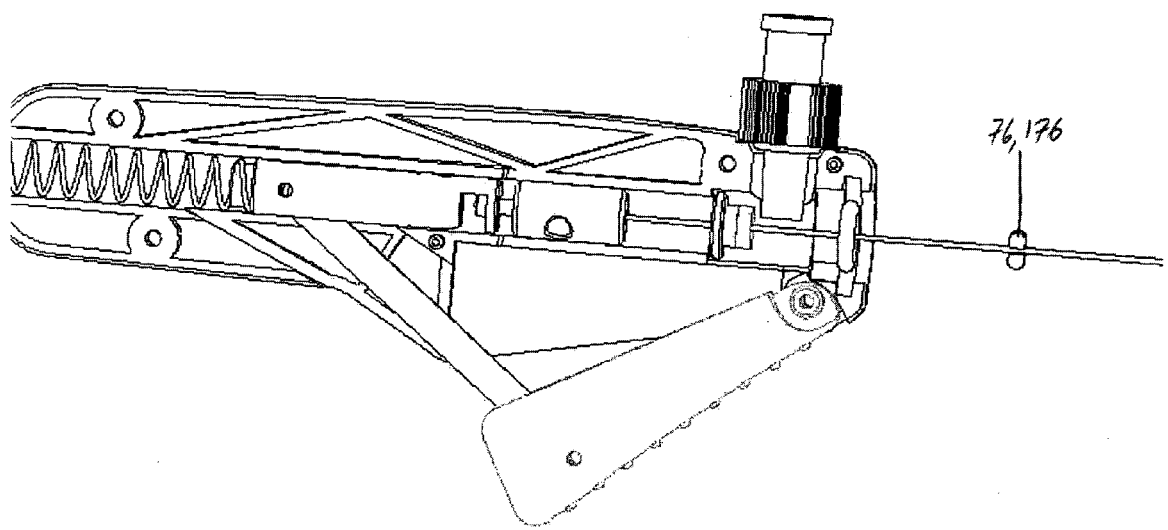
FIG. 14 is a fragmentary, partially longitudinally vertical cross-sectional view of the device actuator of FIG. 13 with the actuation trigger in a first intermediate position and with the proximal portion removed.
Figure 15:
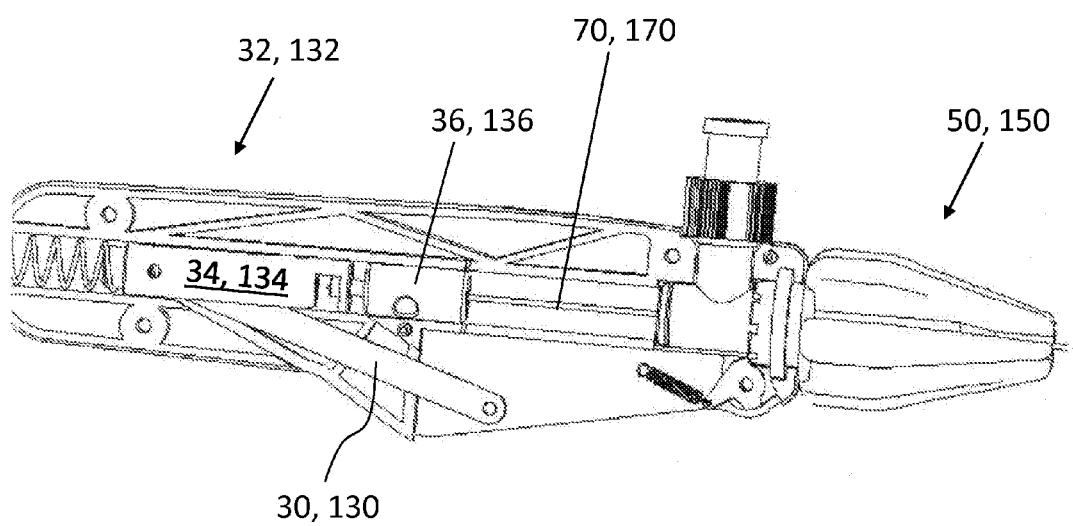
FIG. 15 is a fragmentary, partially longitudinally vertical cross-sectional view of the device actuator of FIG. 13 with the actuation trigger assembly in a closed position and with the trigger removed.

FIGS. 13 to 15 illustrate the movement of the trigger 40, 140 to cause proximal movement of the actuation wire 70, 170 in both of the handle configurations 1, 100. As can be seen in these figures and in FIGS. 16 to 17, the trigger 40, 140 is associated with a nose lock-out assembly 60, 160 at the pivot point of the trigger 40, 140. It is noted that the pivot pin attaching the trigger link 30, 130 to the trigger piston 34, 134 is not illustrated in FIGS. 13 to 15.

FIG. 13 illustrates the trigger 40, 140 in the opened position. This opened position is ensured and maintained when the trigger 40, 140 is not actuated by the presence of a trigger biasing device 32, 132. In the exemplary embodiment shown, this biasing device 32, 132 is a compression spring that is pre-biased in compression and exerts a distally directed force against a trigger piston 34, 134 that is pivotally connected to the proximal end of the trigger link 30, 130. Thus, to depress the trigger 40, 140, the prebiasing force of the spring 32, 132 must be overcome by the user.

The proximal end of the trigger link 30, 130 is pivotally connected to the proximal end of the trigger piston 34, 134 and the distal end of the trigger link 30, 130 is pivotally connected to the end of the trigger 40, 140 opposite the pivot point of the trigger 40, 140. Thus, depression of the trigger 40, 140 causes the cylindrical trigger piston 34, 134 to move proximally within the correspondingly cylindrical piston chamber 16, 116 and, when longitudinally connected to the actuation wire 70, 170, to actuate the actuation wire 70, 170 by moving it in the proximal direction. It is noted that the described configuration provides a trigger that applies a non-linear force to the trigger piston 34, 134. In other words, the squeeze lever linkage provides a non-linear, increasing mechanical advantage as the lever 40, 140 is squeezed by the user.

As can be seen in FIGS. 13 to 15, the link between the actuation wire 70, 170 and the trigger piston 34, 134 is not direct. Instead, as mentioned above, the trigger piston 34, 134 is rotationally disconnected from the actuation wire 70, 170. In handles such as the devices 1, 100 of the present invention, it is desirable to rotate the end effector 200 without rotating the handle body casing 10, 110. Thus, the rotating nose 50, 150 is provided. Also provided for this particular connection is a slider 36, 136 that is similarly cylindrical and slides within the piston chamber 16, 116 longitudinally. The slider 36, 136 is rotationally and longitudinally fastened to the actuation wire 70, 170 by, for example, a set screw that presses against the actuation wire 70, 170 when thread through a central bore of the slider 36, 136. In such a configuration, both the slider 36, 136 and the actuation wire 70, 170 remain centered within the piston chamber 16, 116 but still longitudinally and rotationally movable therein. The proximal end of the slider 36, 136 and the distal end of the trigger piston 34, 134 form the longitudinally fixed but rotationally free connection between the piston 34, 134 and the actuation wire 70, 170. However, as is apparent from the progression of FIGS. 13 to 14, there exists a space (or play) 38, 138 preventing movement of the slider 36, 136 for a short distance when the trigger 40, 140 is first depressed. This connection can be embodied in any way to carry out the function. The connection is illustrated in an exemplary embodiment in the figures of the drawings as a U-shaped fork extending distally with tines pointing downwards (as viewed in the figures) from the distal end of the trigger piston 34, 134 around a mushroom-shaped boss 39 extending proximally from the proximal end of the slider 36, 136. (See, in particular, the cross-section of FIG. 18.) With the inside diameter of the fork being slightly larger than the outer diameter of the mushroom shaft, the slider 36, 136 can rotate freely within the tines of the fork but remains longitudinally connected after the piston closes the space 38, 138.

The space 38, 138 is provided to assist the nose lock-out assembly 60, 160. While the assembly 60, 160 is apparent in FIG. 15, it is highlighted in the enlarged views shown in FIGS. 16 to 17. The lock-out assembly 60, 160 includes a pivoting key 62, 162 that rotates about the same pivot axis as the trigger 40, 140 but is not rotationally fixed with respect to the trigger 40, 140. The key 62, 162 has a tab that is connected to one end of a bias device 64, 164 (a tension spring in the illustrated exemplary embodiment) and the other end of the bias device 64, 164 is connected to a boss on the inside of the trigger 40, 140. In such a configuration, the key 62, 162 is biased to rotate in a clockwise direction with respect to FIGS. 16 to 17. A key stop 66, 166 is positioned on the inside of the trigger 40, 140 to prevent the key from so rotating when the trigger 40, 140 is in the open (rest) position (shown, for example, in FIG. 16). Thus, when the trigger 40, 140 is unactuated, the nose 50, 150 can rotate freely. The key 62, 162 also has a locking tab 68, 168 that performs a locking function when inserted in between the castellations of the castellated ring 59, 159. The key 62, 162 is positioned next to the castellated ring 59, 159 so that the initial depression of the trigger 40, 140 will allow the key 62, 162 to rotate about its axis and press the locking tab 68, 168 against the castellated ring 59, 159. If one of the spaces between the castellations happens to be resting in line with the locking tab 68, 168 so that the tab 68, 168 enters the space, the locking assembly 60, 160 will have performed its locking function and prevent any rotation of the nose 50, 150 while the actuation wire 70, 170 is moved. Alternatively, if no space between the castellations is in line with the locking tab 68, 168, the clockwise force acting upon the key 62, 162 remains throughout the time of trigger stroke; thus, any small rotation of the nose 50, 150 in either direction when the trigger 40, 140 is depressed will force the locking tab 68, 168 to enter the space most adjacent to the locking tab 68, 168. As such, the lock-out assembly 60, 160 prevents any rotation of the nose 50, 150 when the end effector 200 is being actuated or only allows a small amount of rotation of the nose 50, 150—the amount being insignificant to adversely affect the procedure that is being carried out by the end effector 200.

Selection of the castellation size and, therefore, the spacing between the spaces, will determine the permitted rotation of the nose 50, 150 when the trigger 40, 140 is depressed. The illustrated embodiment of eight spaces is only exemplary and can be any desired amount. In this embodiment, the center-points of adjacent spaces are 45 degrees apart from one another. Assuming that the width of the locking tab 68, 168 is substantially equal to the width of the spaces, the most that the nose 50, 150 could rotate if the locking tab 68, 168 was not within a space is, therefore, less than 45 degrees. The locking tab 68, 168 is, however, envisioned to be substantially thinner than the width of the spaces between the castellations. Therefore, the amount of possible nose rotation when the trigger 40, 140 is depressed is substantially less than 45 degrees in an 8-space castellated embodiment.

The longitudinal space 38, 138 between the fork of the trigger piston 134 and the mushroom boss 39 of the slider 36, 136 is sized to be greater than the initial depression of the trigger 40, 140 sufficient to move the locking tab 68, 168 into its locking position before the actuation wire 70, 170 moves longitudinally in any amount.

Figure 16:
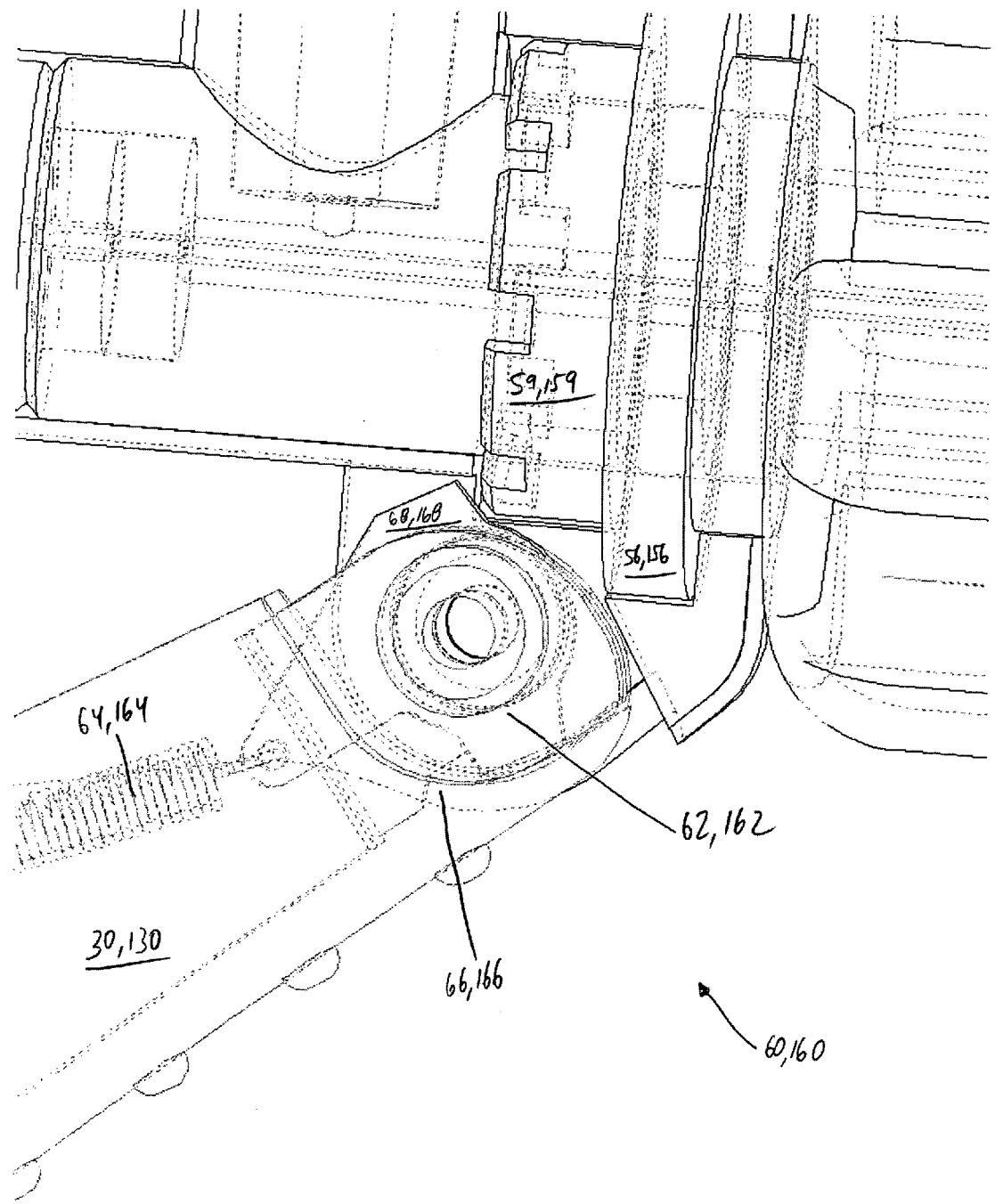
FIG. 16 is an enlarged, hidden line perspective view of a lock-out assembly of the device actuator of FIG. 13 in the open position of the trigger.
Figure 17:
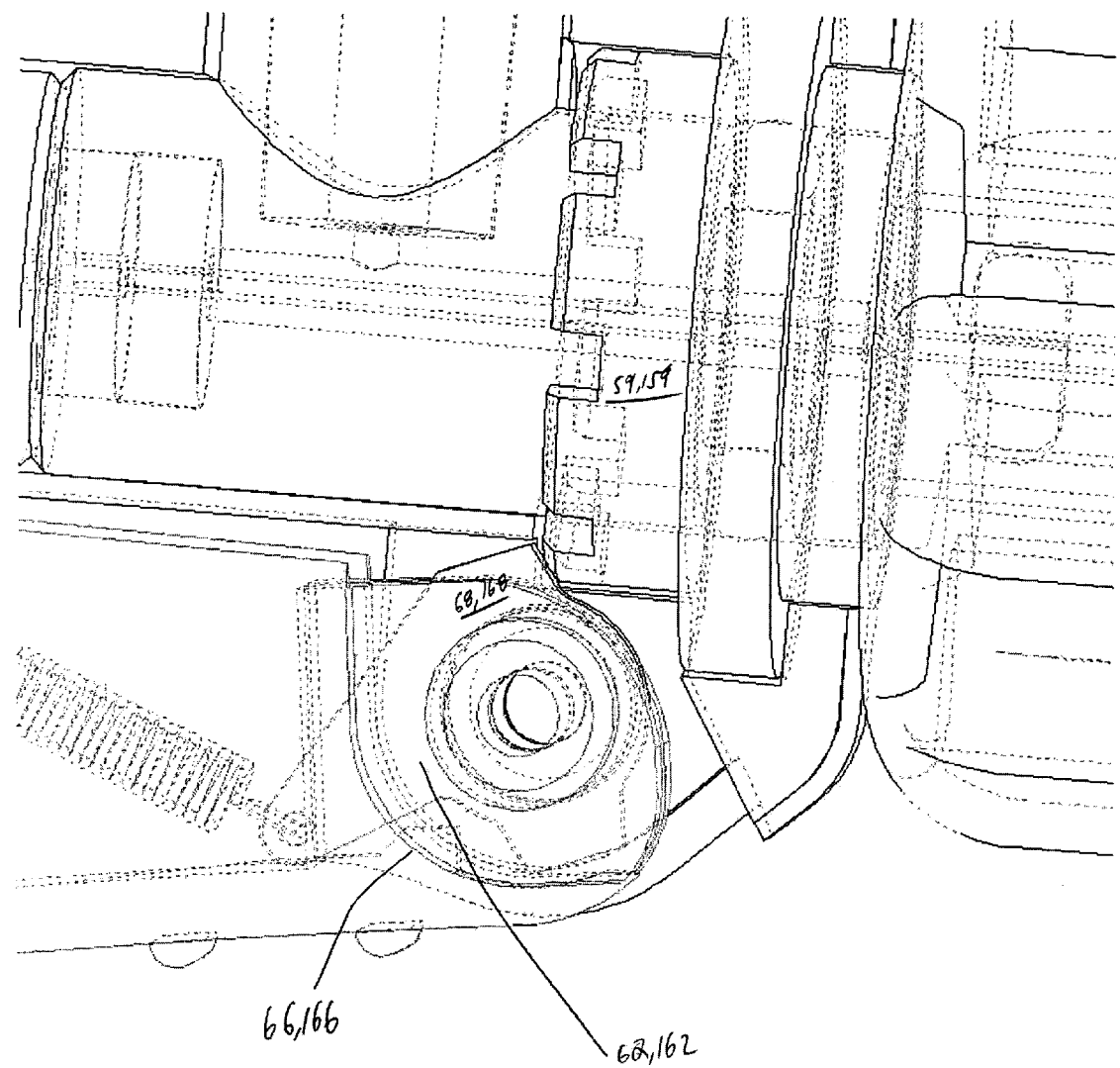
FIG. 17 is an enlarged, hidden line perspective view of the lock-out assembly of FIG. 16 in the closed position of the trigger before the lock engages a castellation space.

FIG. 16 and illustrates the trigger 40, 140 in the open (rest) position and the key stop 66, 166 preventing clockwise movement of the key 62, 162. In comparison, FIG. 17 illustrates the trigger in the fully depressed position so that the key 62, 162 is in the orientation where it is pressing against the castellated ring 159 and is ready to enter any one of the two adjacent spaces when the nose 50, 150 is rotated in either direction.

Figure 18:
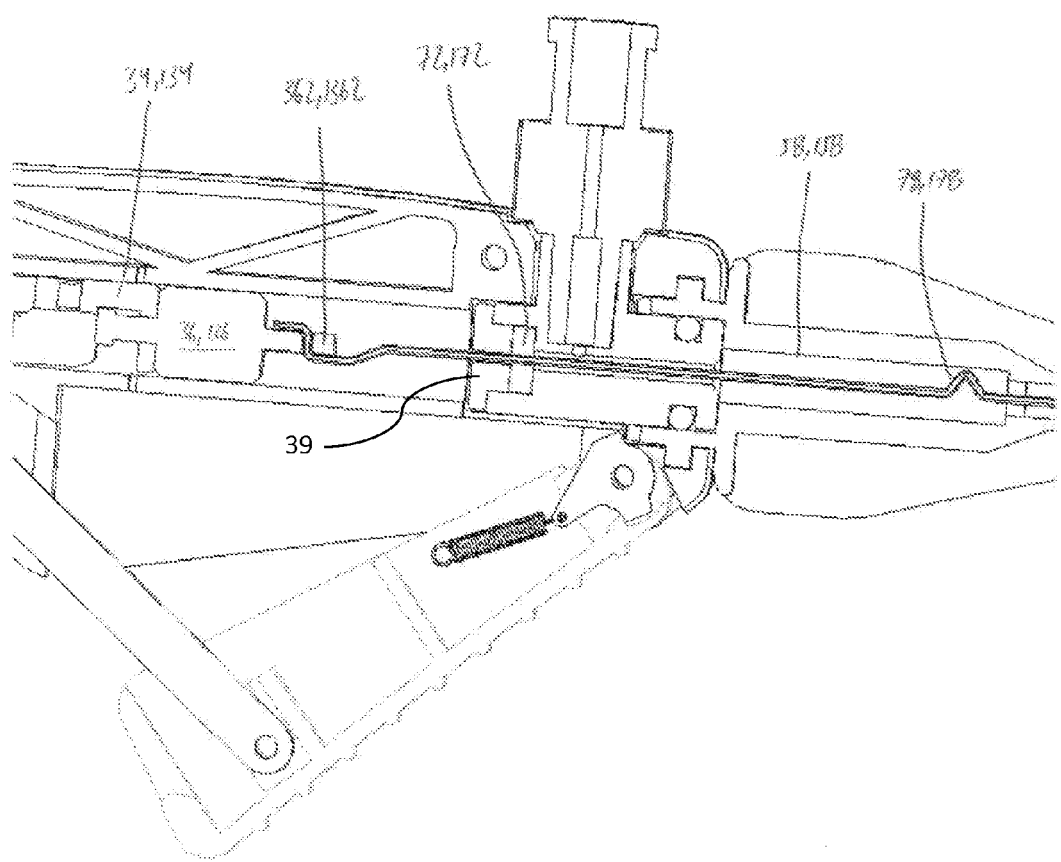
FIG. 18 is a fragmentary, longitudinally vertical cross-sectional view of a distal portion of the device actuator with a z-bend embodiment of the actuation wire and the trigger in the open position.
Figure 19:
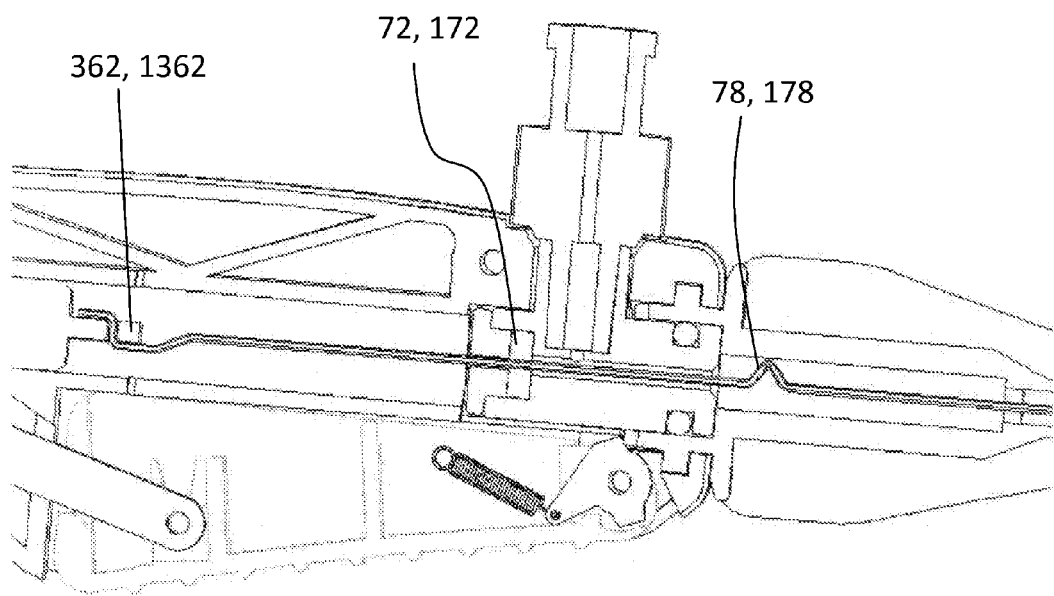
FIG. 19 is a fragmentary, longitudinally vertical cross-sectional view of the distal portion of FIG. 18 with the trigger in a closed position.

FIGS. 18 to 19 illustrate a second exemplary embodiment of the connection and rotational coupling features of the actuation wire 70, 170. Here, the torque puck 76, 176 is replaced by a bend 78, 178 in the actuation wire 70, 170. The height of the torque groove 58, 158 is dependent upon the transverse height of the bend 78, 178 and is sized to be larger than this transverse height so that there is no or no significant friction between the bend 78, 178 and the torque groove 58, 158. In such a configuration, as the wire 70, 170 is rotated, the nose 50, 150 will rotate and, conversely, as the nose 50, 150 is rotated, the wire 70, 170 rotates correspondingly. FIGS. 17 to 18 also reveal a second exemplary embodiment of the connection between the proximal end of actuation wire 70, 170 and the slider 36, 136. A tab 362, 1362 with a through-bore is disposed on the distal end of the slider 36, 136 to receive a Z-bend of the proximal end of the actuation wire 70, 170. In this embodiment, the freely rotating slider 36, 136 can be connected to the actuation wire 70, 170 in a rotatingly fixed manner without impairing the rotatability of the slider 36, 136.

The progression of FIGS. 18 to 19 shows the trigger 40, 140 in its two extreme positions: open/unactuated (FIG. 18) and closed/fully actuated (FIG. 19). Like FIG. 17, FIG. 19 shows the key 62, 162 in the locked orientation but not in one of the spaces of the castellated ring 59, 159; a small rotation of the nose 50, 150 will cause the key 62, 162 to drop into one of the two adjacent spaces.

Figure 20:
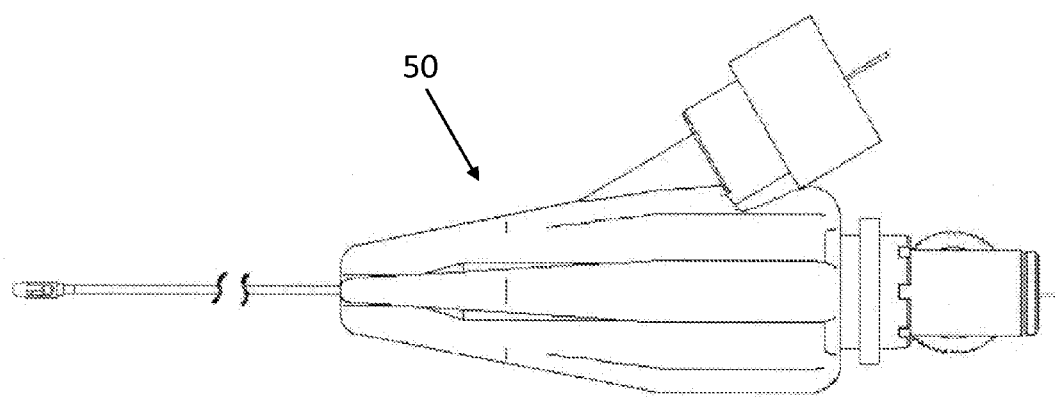
FIG. 20 is a fragmentary, bottom elevational view of the end effector and a proximal portion of the device actuator of FIG. 1 with the side guidewire port.

FIG. 20 illustrates the sub-assembly associated with the nose 50, 150 and a diagrammatic illustration of an end effector 200.

Figure 21:
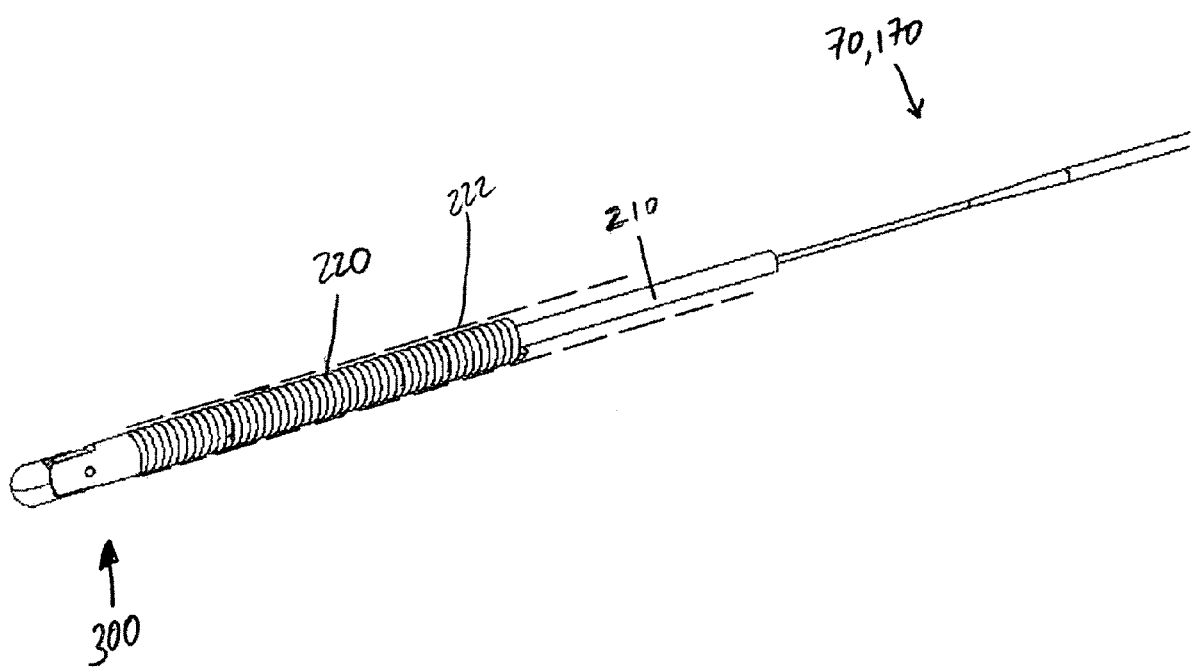
FIG. 21 is a fragmentary, partially broken away perspective view of a first embodiment of the end effector of FIG. 20 viewed from the side of a distal end thereof.

FIGS. 21 to 26 illustrate a first exemplary embodiment of an end effector 300. Attachment of this end effector 300 to the handle 1, 100 of the present invention is illustrated in FIG. 21. As can be seen therein, the actuation wire 70, 170 tapers from a relatively thicker diameter proximally to a relatively thinner diameter distally. This taper can begin and end at any point along the actuation wire 70, 170. Having a thinner diameter at the distal end near the end effector 200 allows the area of thinness to be more flexible. Having the thinner diameter throughout most of the shaft length up to the end effector 200 increases the torqueability of the end effector 200 with respect to the handle 1, 100.

Also visible in FIG. 21 is an inner sheath 210 disposed between the actuation wire 70, 170 and the coil 220. The inner sheath 210 can be provided to reduce or limit the friction that could be caused by rubbing against the interior of the coil 220. As such, the inner sheath 210 is made from a friction reducing material, such as TEFLON® or PTFE. The outer sheath 222 is illustrated diagrammatically by dashed lines in FIG. 21. This outer sheath 222 is made of a material such as Polyurethane or PEBAX™.

Figure 22:
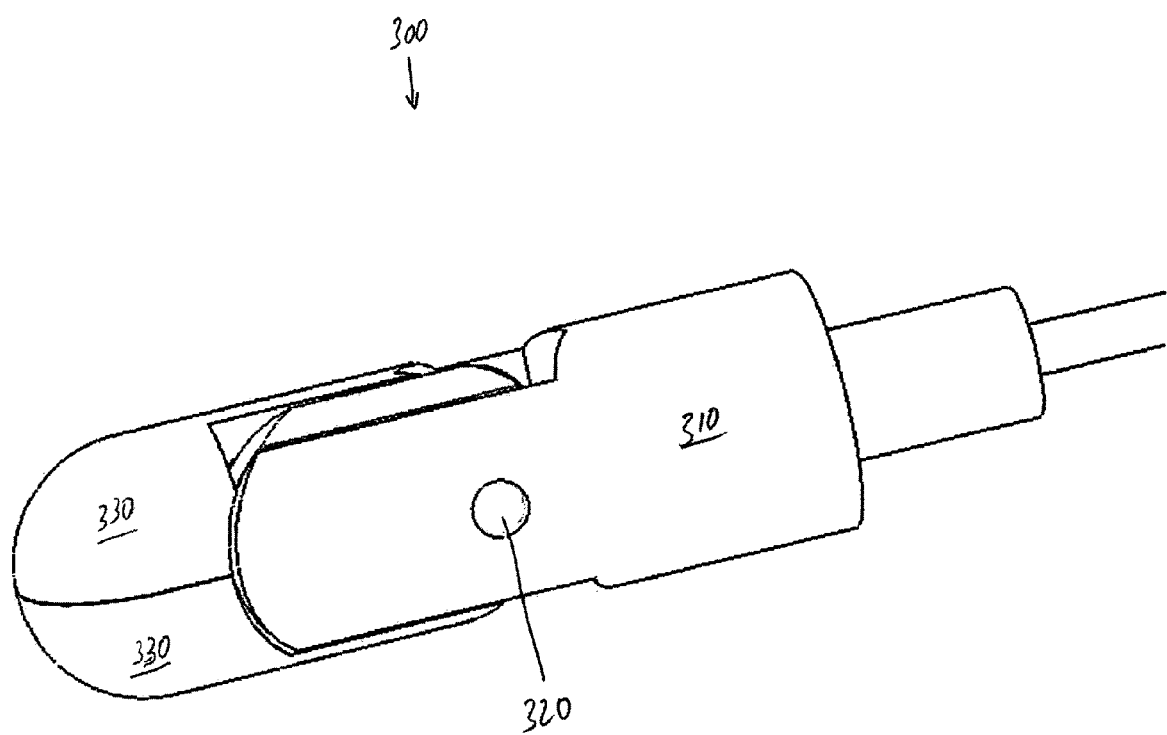
FIG. 22 is a fragmentary, enlarged partially broken away perspective view of the end effector of FIG. 21 with the jaws in a closed position.
Figure 23:
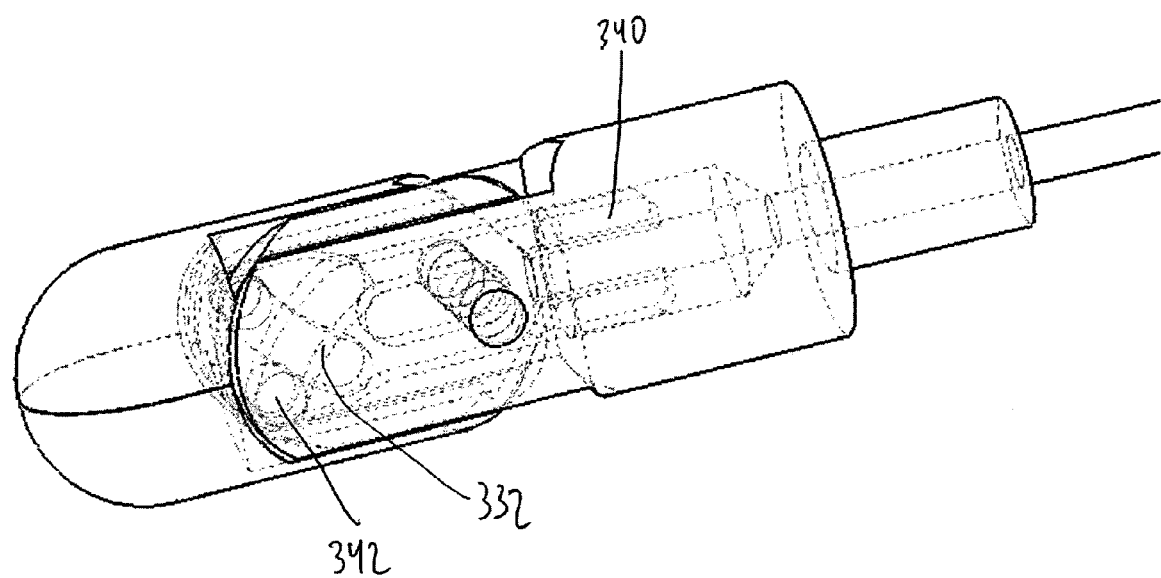
FIG. 23 is an enlarged, fragmentary, hidden line perspective view of the end effector of FIG. 21.
Figure 24:
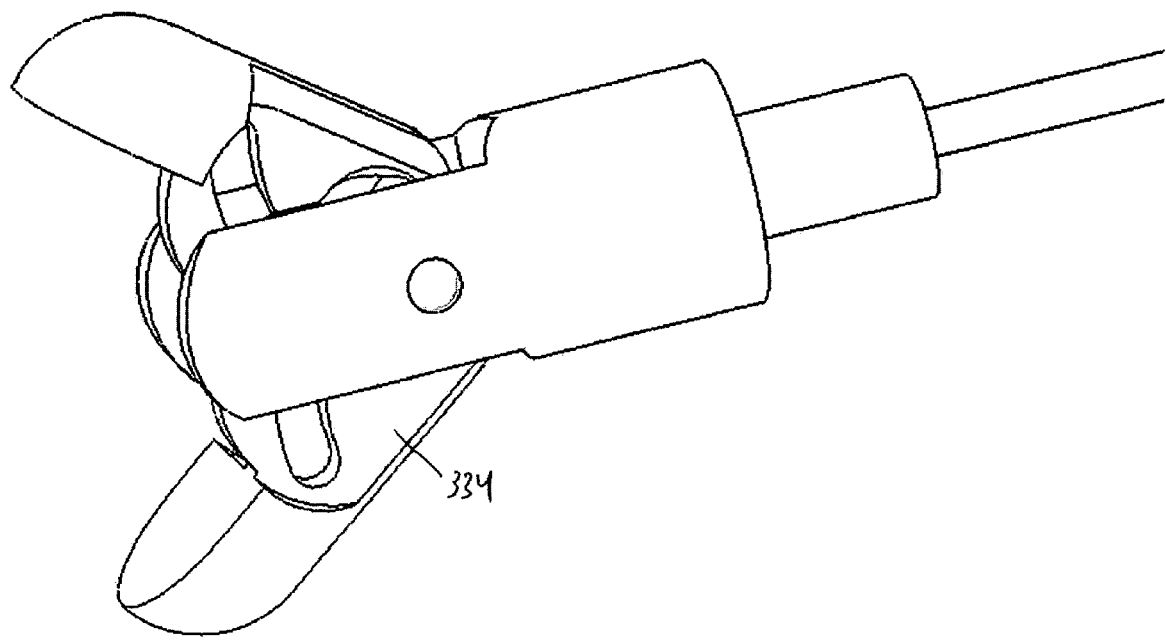
FIG. 24 is a fragmentary, enlarged partially broken away perspective view of the end effector of FIG. 21 with the jaws in an open position.
Figure 25:
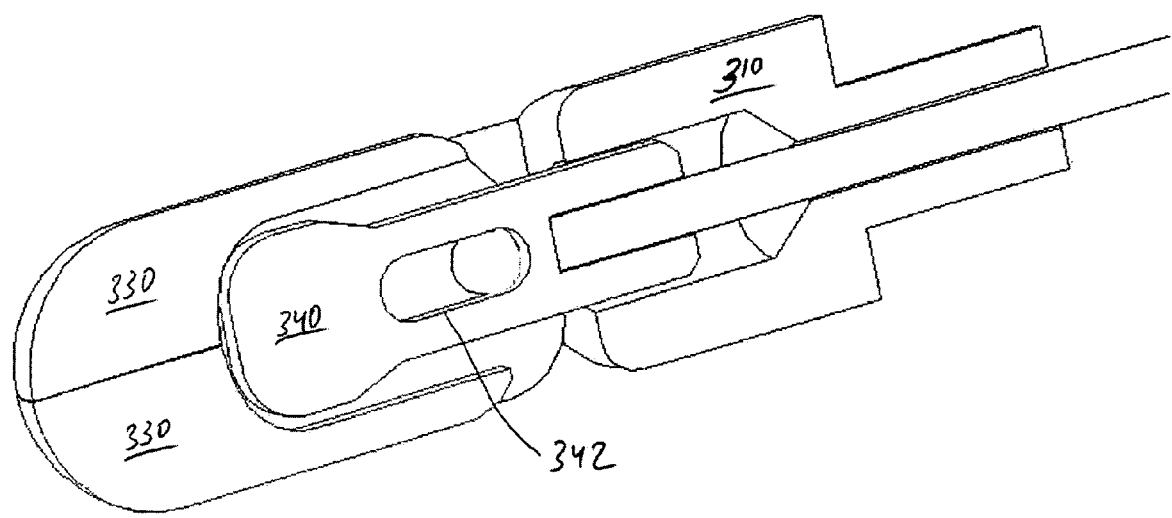
FIG. 25 is a longitudinally vertical cross-sectional view of the end effector of FIG. 21.
Figure 26:
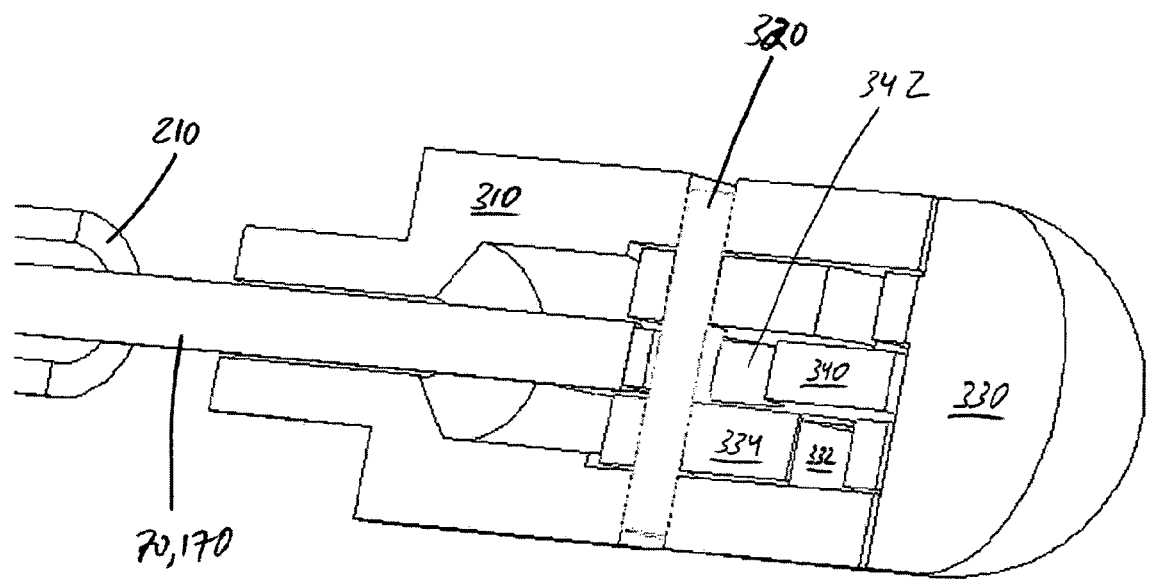
FIG. 26 is a longitudinally horizontal cross-sectional view of the end effector of FIG. 21.

FIG. 22 shows the entire end effector 300 having a clevis 310, a clevis pivot pin 320, and two jaws 330. The hidden line view of FIG. 23 shows the actuator cam 340 and one of two cam pins 342, each of which slides respectively within a cam surface 332 of one of the jaws 330, the cam surface 332 being a curved groove in the tang 334 of each jaw 330. The view of FIG. 24 shows the jaws 330 in an open position with the cam pin 342 at the other extreme of the cam surface 332. The cross-sectional views of FIGS. 25 to 26 reveals other features of the actuator cam 340. For example, the actuator cam 340 has a cam surface 342 in the shape of a linear longitudinal groove surrounding the clevis pivot pin 320 that causes the jaws 330 to open when the actuator cam 340 is moved in a proximal direction and to close when the actuator cam 340 is moved in a distal direction.

FIGS. 27 to 31 illustrate a second exemplary embodiment of an end effector 400 that is used with the guidewire 182. Attachment of this end effector 400 to the handle 1, 100 of the present invention can be similar to that illustrated in FIG. 21.

Figure 27:
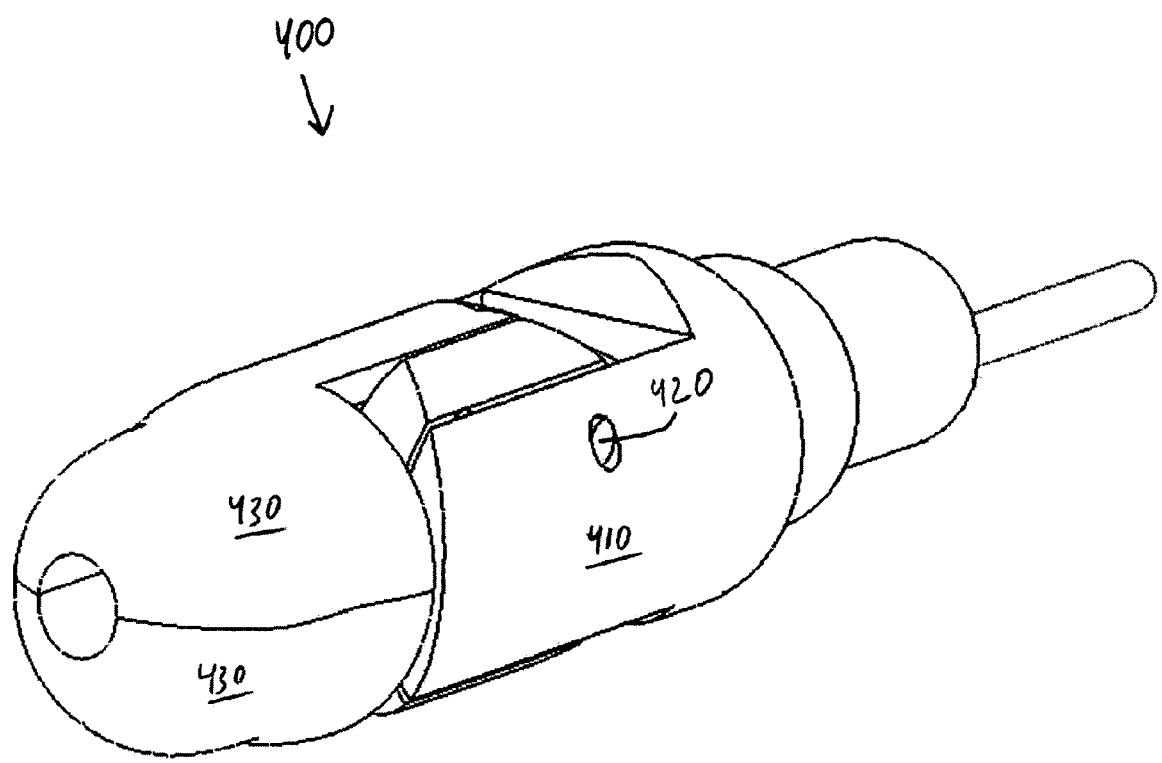
FIG. 27 is a fragmentary, partially broken away perspective view of a second embodiment of the end effector of FIG. 20 viewed from the side of a distal end thereof with the jaws in a closed position.
Figure 28:
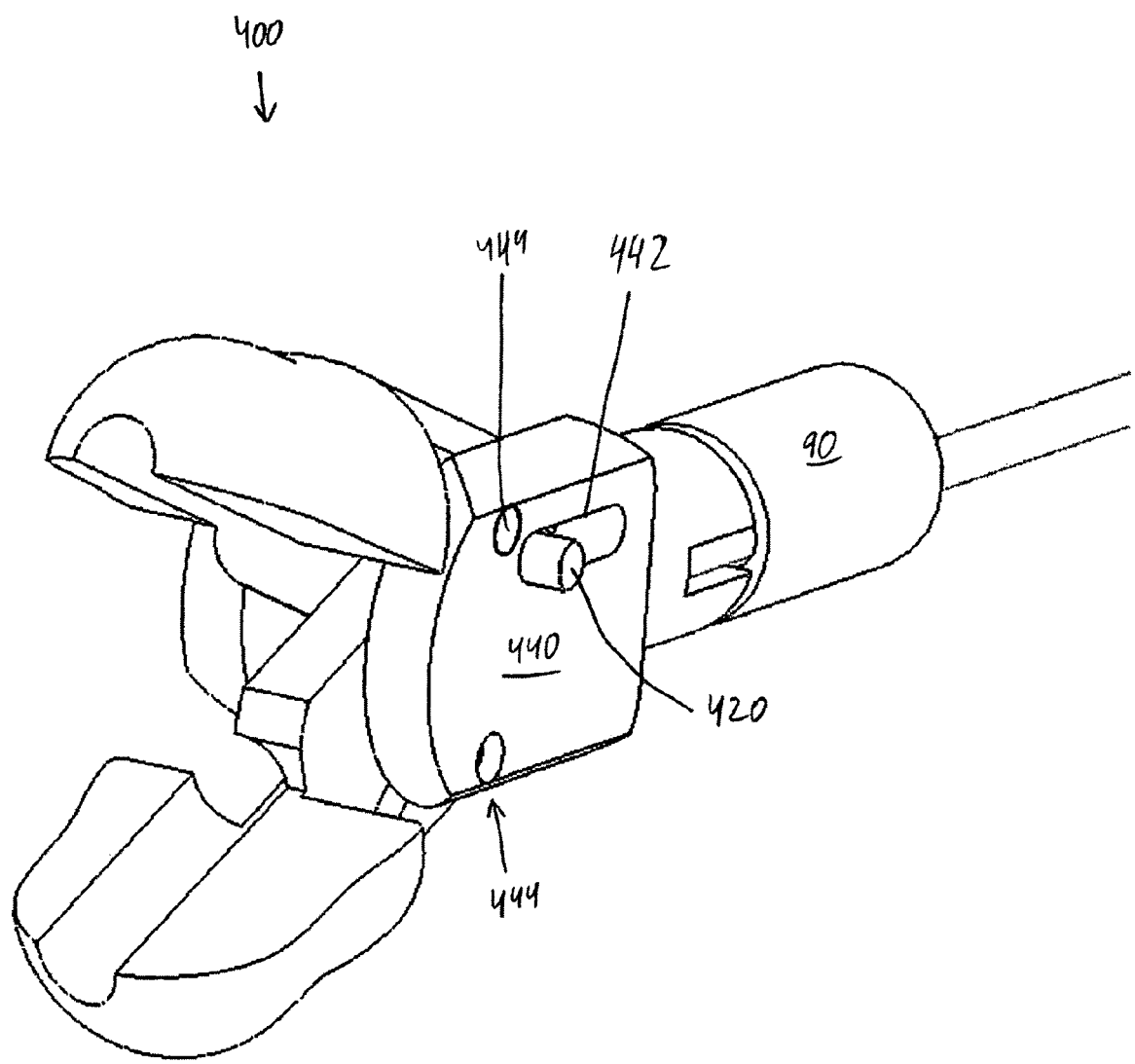
FIG. 28 is a fragmentary, enlarged partially broken away perspective view of the end effector of FIG. 27 with the jaws in an open position and with the clevis removed.
Figure 29:
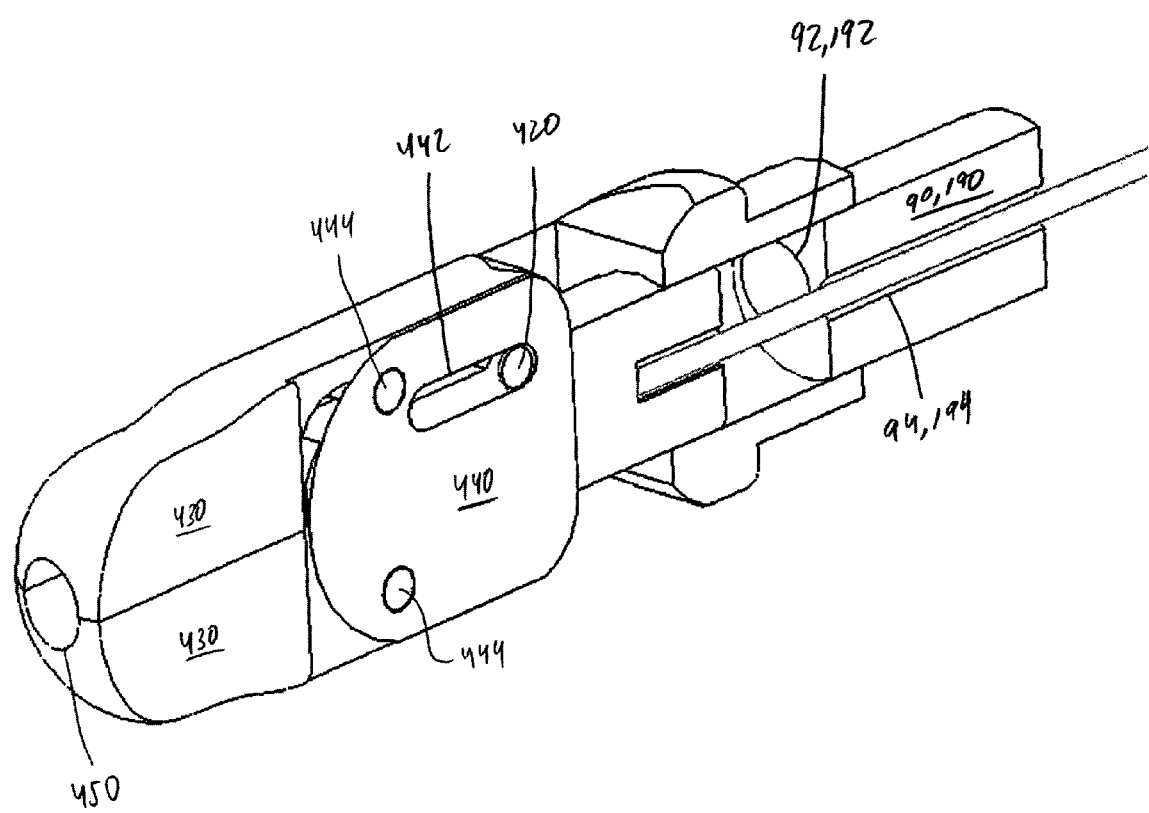
FIG. 29 is a fragmentary, enlarged, partially broken away and longitudinally vertical cross-sectional view of the end effector of FIG. 27 along an actuation wire axis.
Figure 30:
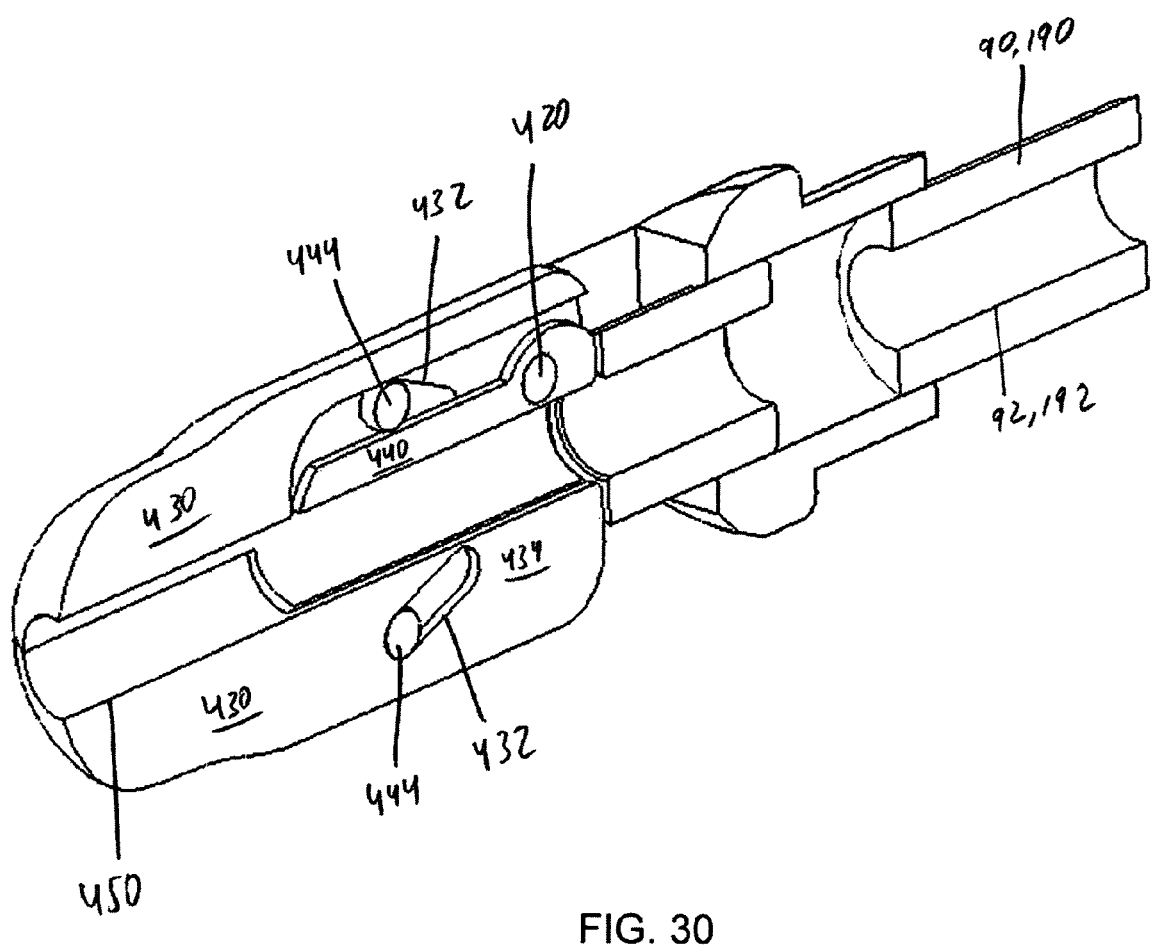
FIG. 30 is a fragmentary, enlarged, partially broken away and longitudinally vertical away cross-sectional view of the end effector of FIG. 27 along a guidewire axis.
Figure 31:
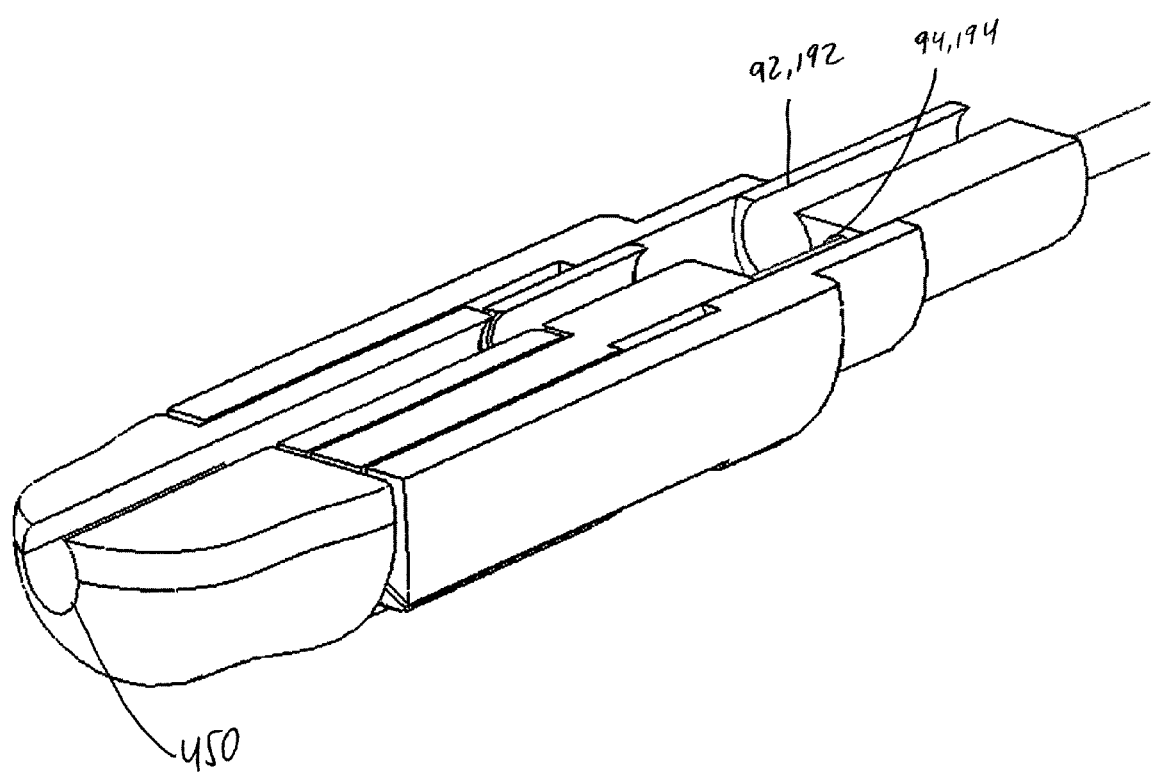
FIG. 31 is a fragmentary, enlarged, partially broken away and longitudinally horizontal cross-sectional view of the end effector of FIG. 27.

FIG. 27 shows the entirety of the end effector 400, which includes a clevis 410, a clevis pivot pin 420, and two jaws 430. The view of FIG. 28 shows the actuator cam 440 and one of two cam pins 444 (the lower cam pin 444 is not illustrated). As illustrated in FIG. 30, each of the cam pins 444 slides respectively within a cam surface 432 of one of the jaws 430. The cam surface 432 is, in this exemplary embodiment, a linear groove in the tang 434 of each jaw 430. The groove is disposed at an angle to the axis of the actuation wire 70, 170 so that travel of the pin 444 within the cam surface 432 causes the respective jaw to pivot out of alignment with the axis of the end effector 400 (i.e., opening of the jaw). The view of FIG. 28 shows the jaws 430 in this open position. The cross-sectional views of FIGS. 29 to 30 reveal other features of the actuator cam 440. For example, the actuator cam 440 includes a cam surface 442 shaped as a linear longitudinal groove in which is disposed the circular clevis pivot pin 420. The actuator cam 440 also includes a cam pin 444 for each of the jaws 430, which pin 444 travels within the cam surface 432 of the respective jaw 430. This configuration of cam pins and surfaces in the jaws 430 and the actuator cam 440 allow the jaws 430 to open when the actuator cam 440 is moved in a proximal direction and to close when the actuator cam 440 is moved in a distal direction (the distal-most position of the cam 440 being shown in FIGS. 29 to 30).

In this second embodiment, the jaws 430 each define one half of a guidewire recess 450. Because both the actuation wire 70, 170 and the guidewire 182 are parallel within the two-lumen tube 90, 190, neither of the wires are centrally disposed within the two-lumen tube 90, 190 (although one can be if desired). Accordingly, the guidewire recess 450 is not aligned with the central axis of the end effector 400. The two lumens 92, 94 for receiving, respectively, the guidewire 182 and the actuation wire 70, 170 are apparent in FIGS. 29 and 31.

In some applications, it is desirable to eliminate the need of threading a guidewire to the site at which the end effector is to be applied in addition to having the shaft (e.g., two-lumen tube 190, inner sheath 210, coil 220, outer sheath 222) of the actuation device at the operation site. If the end effector 200 is already at the site, it is desirable to keep the end effector 200 in place and to use that placement, along with a portion of the shaft of the device, to guide separate devices to the site with the shaft portion serving as the guidewire or exchange wire. The present invention provides various alternatives for removably fixing the end effector 200 to the distal end of the device.

Figure 32:
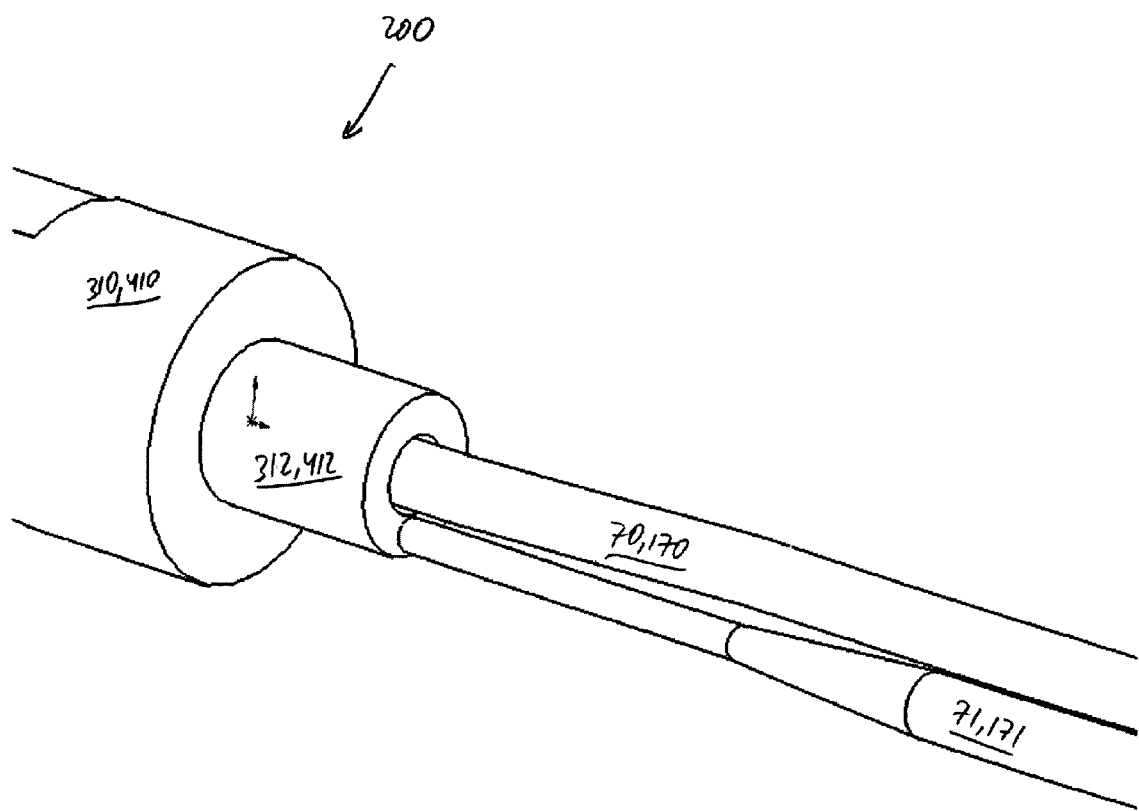
FIG. 32 is a fragmentary, enlarged, partially broken away perspective view of a proximal portion of the end effector of FIG. 27 with a first embodiment of an end effector disengagement device.

An exemplary embodiment for disengaging the end effector 200, 300, 400, 500 from the distal end of the shaft has the actuation wire 70, 170 continues toward (or even out of) the proximal end 18, 118 of the body casing 10, 110. In a configuration where the proximal end of wire 70, 170 is contained entirely within the handle, the wire 70, 170 wraps around a boss in the body casing 10, 110 in a 180 degree bend to form a proximally extending portion 71, 171. In a configuration where the wire 70, 170 exits the proximal end of the body casing 10, 100, then the wire 70, 170 is looped 180 degrees so that a user can place a hand or finger within the center of the loop. The wire 71, 171, then, continues back in the distal direction all the way through the handle and the shaft until it makes contact with the clevis 310, 410 of the end effector 200, 300, 400, 500 as shown in FIG. 32.

Contact with the clevis 310, 410 is removable and removal can be effected by applying a proximally directed force to the proximally extending portion 71, 171 sufficient to break the contact. The portion of the wire 71, 171 adjacent a distal portion 312, 412 of the clevis 310, 410 is narrowed considerably as compared to the width of the actuation wire 70, 170. As such, when the proximally directed force is applied, the break-away portion 71, 170 is broken instead of the actuation portion 70, 170. The break-away portion 71, 171 is, then, removed entirely from the shaft and the handle 1, 100. Because the tension of the folded wire 70, 71, 170, 171 holding the clevis 310, 410 inside the distal end of the shaft is no longer present, the shaft and handle 1, 100 can be entirely removed from the connected end effector 200 and actuation wire 70, 170. The length of the actuation wire 70, 71, 170, 171 can, now, be used as a guidewire or exchange wire for conducting procedures at the operation site.

In the internal loop embodiment, a lever or other mechanical device is connected to the boss and, when breaking of the connection is desired, the lever is moved to place a proximally directed force on the wire 70, 71, 170, 171 and break the contact at the reduced diameter portion 71, 171. In the external loop embodiment, the user places a finger or hand inside the loop and pulls proximally. This force breaks the contact at the reduced diameter portion 71, 171.

FIGS. 33 to 42 illustrate a second exemplary embodiment for disengaging the end effector 500 from the distal end of the shaft. Some of the features of this embodiment are similar to the end effector 300 described above. Therefore, the description of similar features will not be repeated for the sake of brevity.

Figure 33:
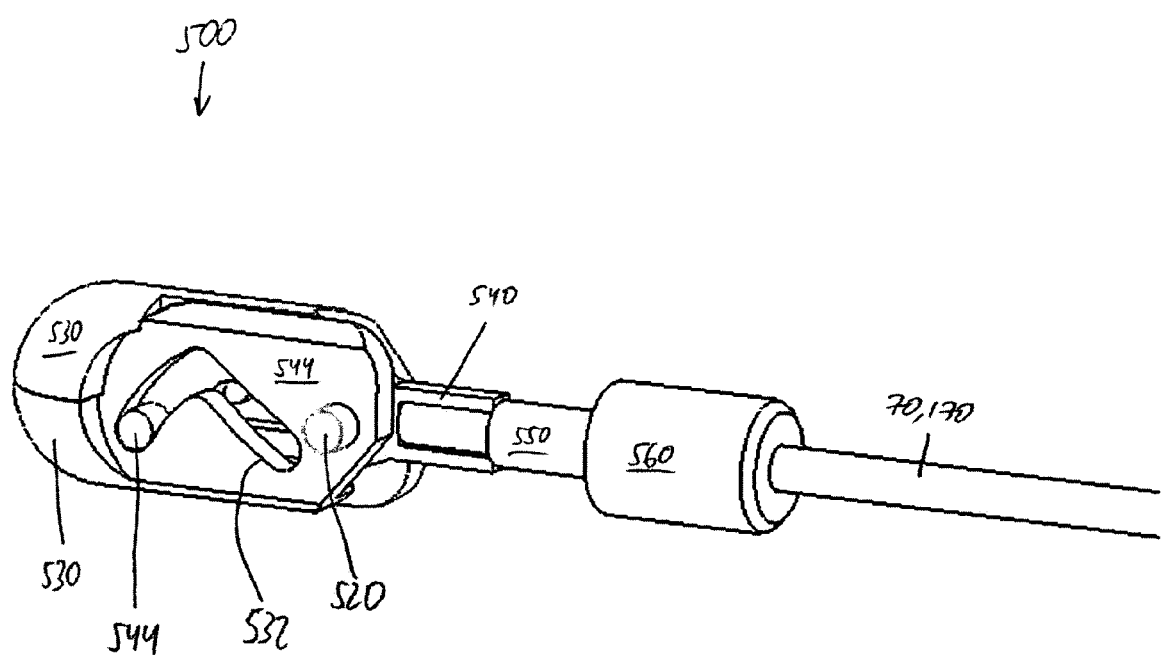
FIG. 33 is a fragmentary, enlarged, partially broken away perspective view of a third embodiment of the end effector of FIG. 20 viewed from the side of a proximal end thereof with the jaws in a closed position and with the clevis removed.

FIG. 33 shows the end effector 500 with a clevis 510, a clevis pivot pin 520, and two jaws 530. Each of the jaws 530 has an L-shaped cam surface 532 within its tang 534 for receiving therein a cam pin 544. The distal portion of the cam surface 532 is similar to the cam surface 532 and is utilized for opening and closing the jaws 530. The proximal portion of the cam surface 532 is added and used for separating the end effector 500 from the shaft, as will be described in further detail below. The actuator cam 540 in this embodiment has, at its proximal end, a hollow fracture piston 550 that surrounds the actuation wire 70, 170. As can be seen best in FIG. 42, protruding from the proximal end of the clevis 510 is a cylindrical, hollow barb 512. A cylindrical hollow fracture tube 560 has an interior cylindrical cavity 562 shaped to fit snugly therein the barb 512. A frangible portion 564 protrudes inwardly from an intermediate location of the interior cylindrical cavity 562. When the fracture tube 560 is at its distal-most position surrounding the barb 512, as shown in FIGS. 34 to 36, and most particularly in FIG. 38, the frangible portion 564 is in line with and protrudes into a groove 514 located between the barb head 516 and barb shaft 518.

Figure 34:
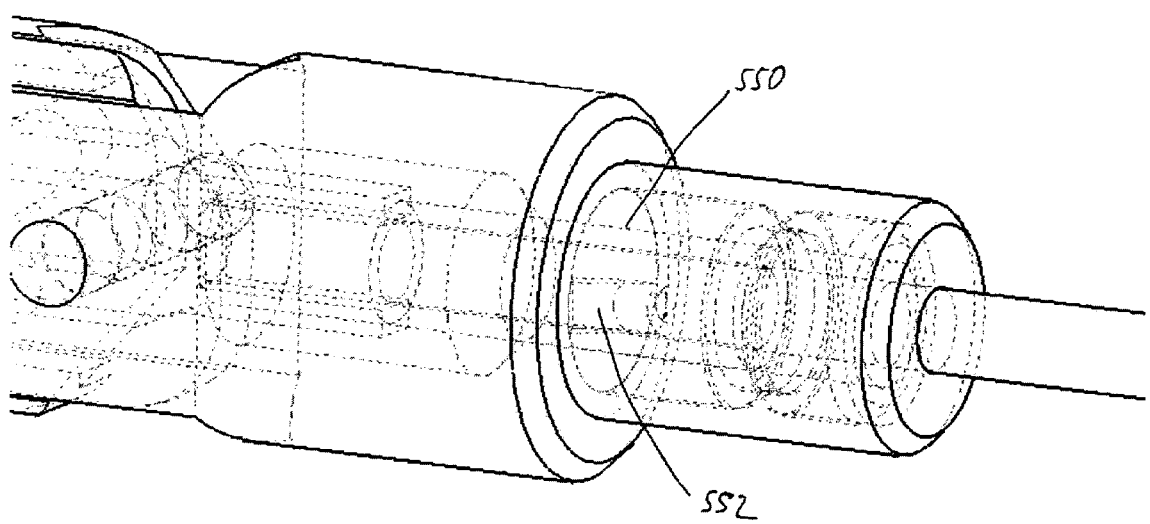
FIG. 34 is a fragmentary, enlarged, partially broken away hidden line perspective view of the end effector of FIG. 33.
Figure 35:
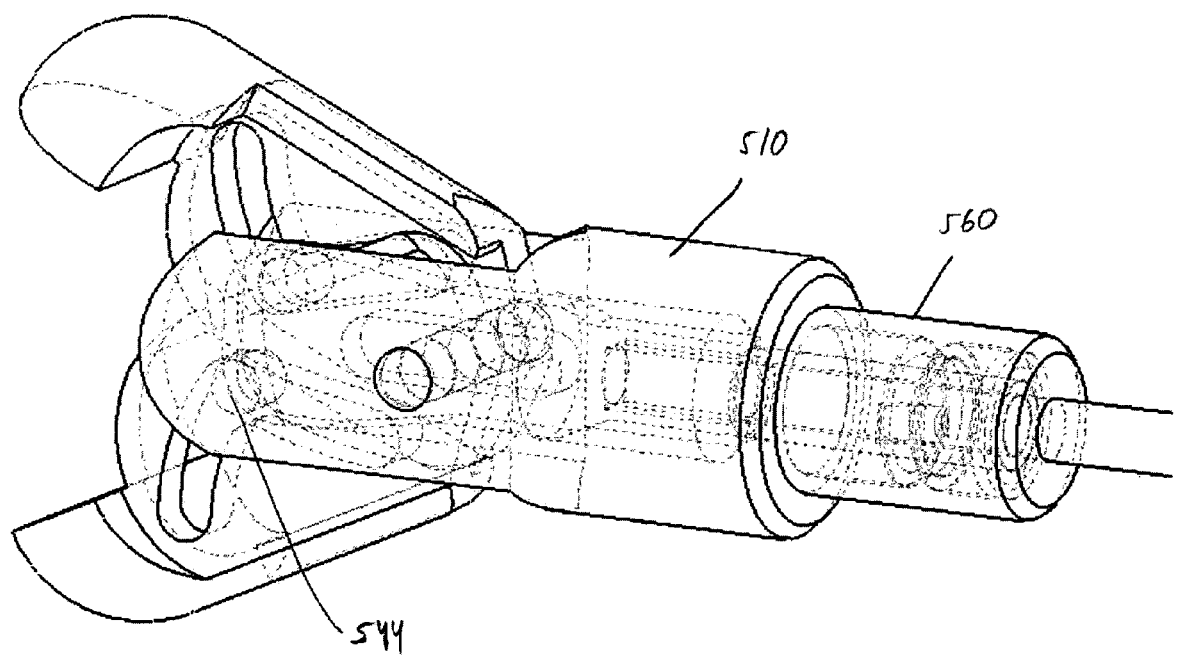
FIG. 35 is a fragmentary, enlarged, partially broken away hidden line perspective view of the end effector of FIG. 33 with the jaws in an open position.
Figure 36:
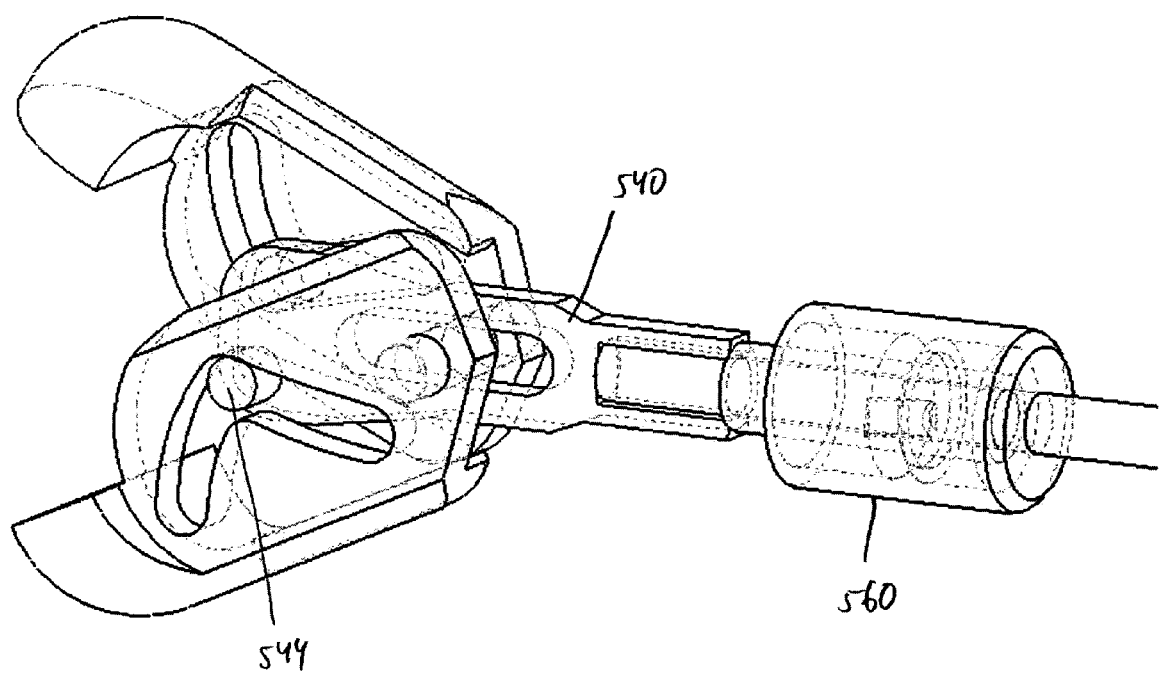
FIG. 36 is a fragmentary, enlarged, partially broken away hidden line perspective view of the end effector of FIG. 35 with clevis portions removed.
Figure 37:
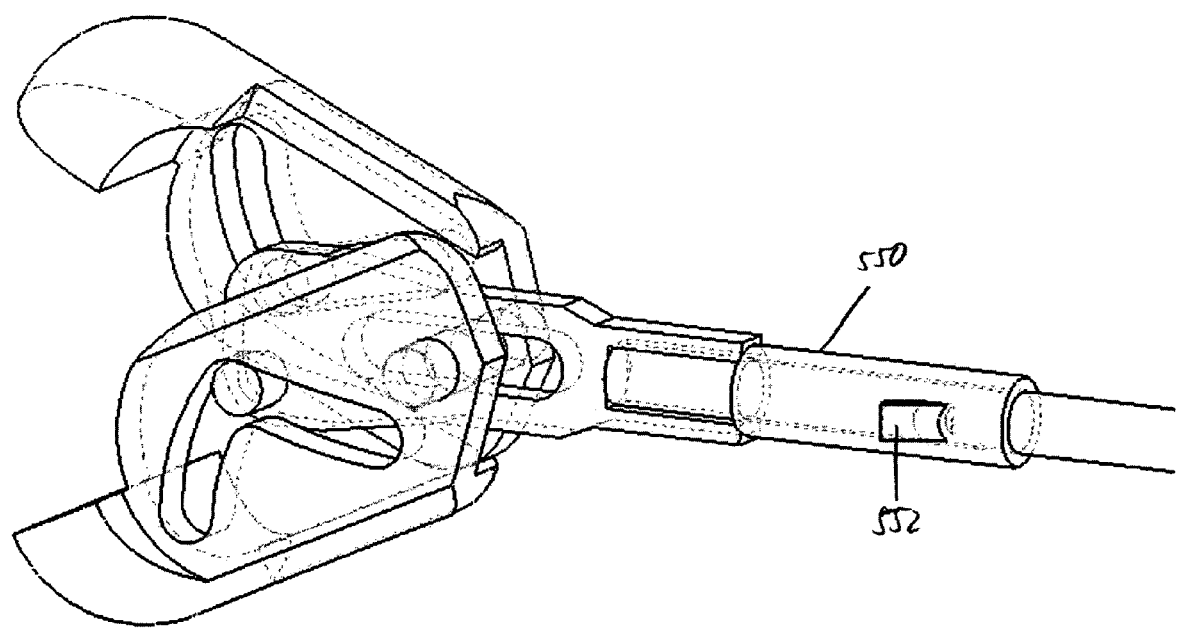
FIG. 37 is a fragmentary, enlarged, partially broken away hidden line perspective view of the end effector of FIG. 36 with a fracturing portion removed.
Figure 38:
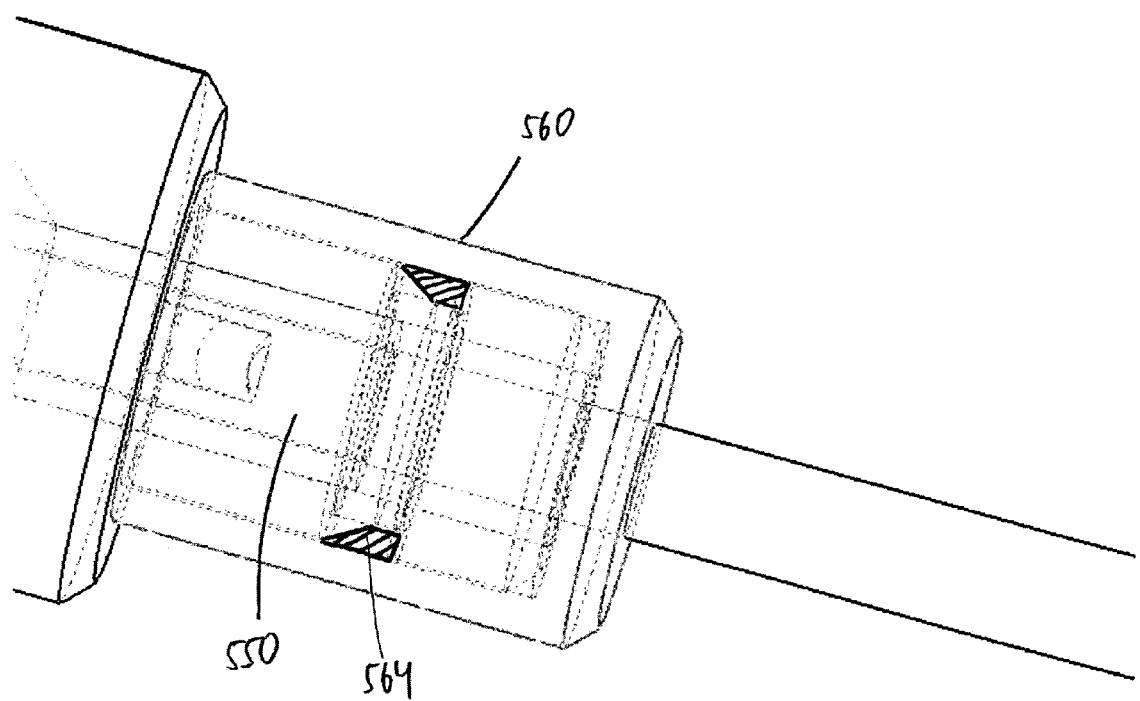
FIG. 38 is a fragmentary, further enlarged, partially broken away hidden line perspective view of the end effector of FIG. 35.
Figure 42:
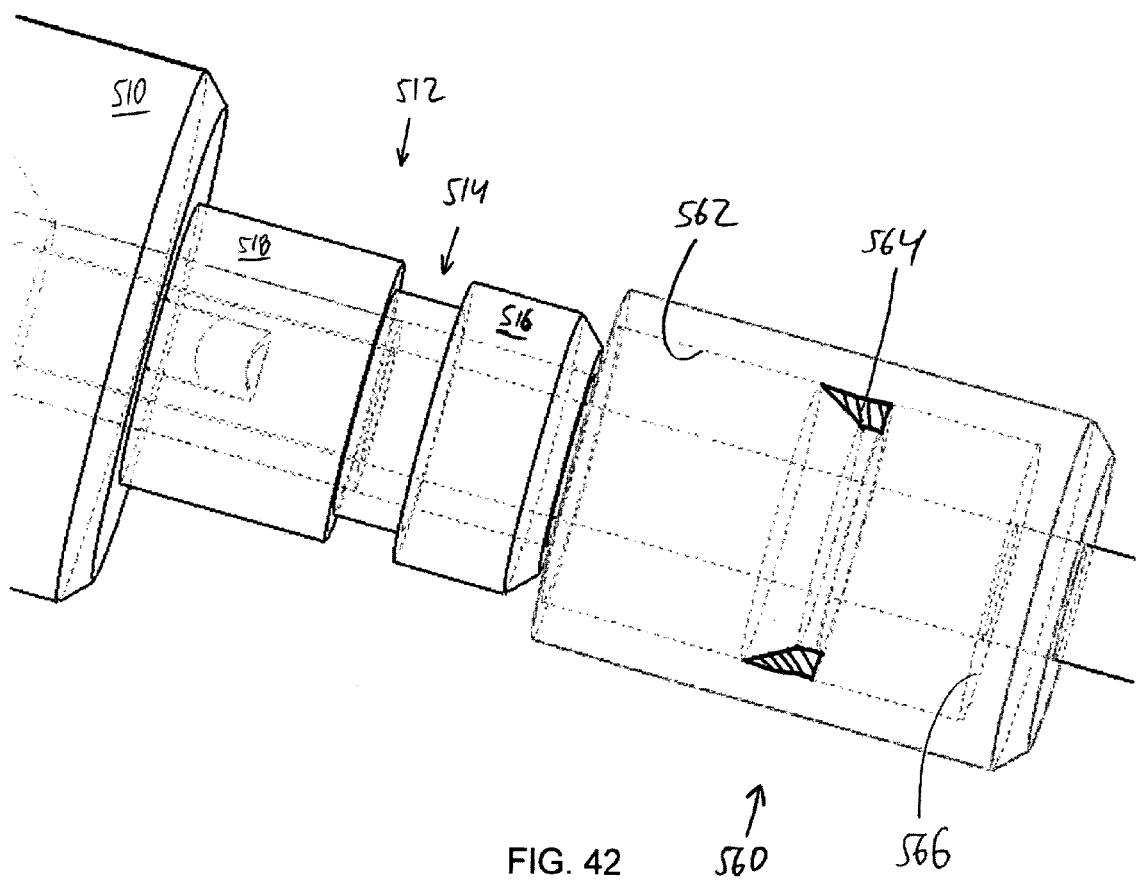
FIG. 42 is a fragmentary, further enlarged, partially broken away hidden line perspective view of the end effector of FIG. 41 and with the fracturing portion in a fourth fracturing position.

FIG. 34 illustrates the orientation of the fracture piston 550 when the jaws 530 are in the closed position of the end effector 500 and FIGS. 35 to 37 illustrate the orientation of the fracture piston 550 when the jaws 530 are in the open position of the end effector 500. In the open position illustrated in FIGS. 35 to 37, the location of the cam pin 544 corresponds to the jaws-open position within the L-shaped cam surface 532. In this position, the cam pin 544 rests at the angle/middle point of the cam surface 532. The clevis 510 is removed in FIG. 36 to better reveal the features of the jaws 530 and the actuator cam 540 disposed therein. The fracture tube 560 is removed in FIG. 37 to better reveal the features of the fracture piston 550 and its spring catch 552. FIG. 38 shows the alignment of the features of the fracture tube 560, the fracture piston 550 before the proximal end of the fracture piston 550 hits the proximal transverse wall 566, which is the stop limit for proximal movement of the fracture piston 550 within the fracture tube 560. The proximal transverse wall 566 is best illustrated in FIG. 42.

Removal of the end effector 500 will be described with primary reference to FIGS. 39 to 42. When the user desires to remove the end effector 500 from the distal end of the shaft, a proximally directed force will be imparted on the actuation wire 70, 170 to move the actuation wire 70, 170 further than the position it would be in when the jaws 530 are in the open position, shown in FIGS. 35 to 37. One exemplary embodiment for so moving the actuation wire 70, 170 can be a pivoting lever 600 (see FIG. 2) that is attached to the trigger piston 34, 134 to move the trigger piston 34, 134 against the bias of the spring 32, 132 further proximal in the handle than the proximal-most position of the piston 34, 134 (when the trigger 40, 140 is fully depressed as shown, for example, in FIG. 15). Another embodiment can be a screw 700 (see FIG. 13) threaded into the proximal end of the trigger piston 34, 134 that is screwed to, thereby, move the trigger piston 34, 134 in a similar proximal manner.

Figure 39:
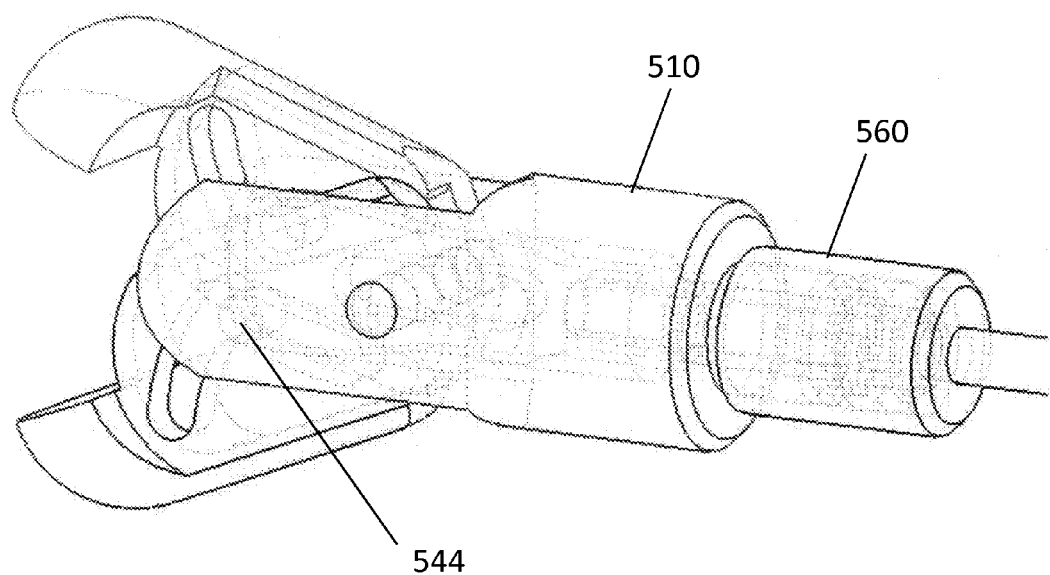
FIG. 39 is a fragmentary, enlarged, partially broken away hidden line perspective view of the end effector of FIG. 35 with the jaws in a first intermediate fracture position and with the fracturing portion in a first fracturing position.

In any configuration, the actuation wire 70, 170 is caused to move the proximal transverse wall 554 of the fracture piston 550 against the proximal transverse wall 566 inside the cavity 562 of the fracture tube 560 and further than the location of the proximal transverse wall 566 shown in FIGS. 34 to 36 and 38. When the fracture piston 550 bottoms out against the proximal transverse wall 566 of the fracture tube 560, a significant proximally directed force is imparted on the fracture tube 560. As shown in FIG. 38 in highlighted cross-section, the only feature preventing the fracture tube 560 from moving in the proximal direction is the frangible portion 564. Because the removal force is significantly greater than the shear strength of the frangible portion 564, the frangible portion 564 shears off from the fracture tube and is left within the barb groove 514 as the remainder of the fracture tube 560 moves proximally. FIG. 39 illustrates the fracture tube 560 as the frangible portion is being sheared off and FIGS. 40 to 41 illustrate the fracture tube 560 after the frangible portion is sheared off and is being removed from the barb 512 into the inside of the coil 220.

It is noted at this point that the fracture tube 560 is no longer attached to the clevis 510 or to the shaft. Being in this unattached state, it is possible for the fracture tube 560 to impermissibly drop into the volume of the operation site of the end effector 500. To prevent this occurrence, the outer diameter of the fracture tube 560 is selected to be slightly larger than the inner diameter of the coil 220. Because the fracture tube 560 is made of a material that is significantly softer than the coil 200, and due to the fact that the proximal removal force is sufficient to deform the outer surface of the fracture tube 560, the removal force creates an interference fit between the coil 220 and the fracture tube 560 sufficient to ensure that the fracture tube 560 is retained within the coil 220. At this point, the handle 1, 100 and the shaft, along with the fracture tube 560, can be removed from the end effector 500 that is longitudinally fixed to the actuation wire 70, 170. In such a state, the actuation wire 70, 170 becomes a guidewire that can be used to guide (from the proximal end thereof) other devices along the actuation wire 70, 170 up to the end effector 500. FIG. 42 illustrates the fracture tube 560 in a position proximal of the barb 512 and with the frangible portion 564 sheared off (indicated by cross-section lines).

Figure 40:
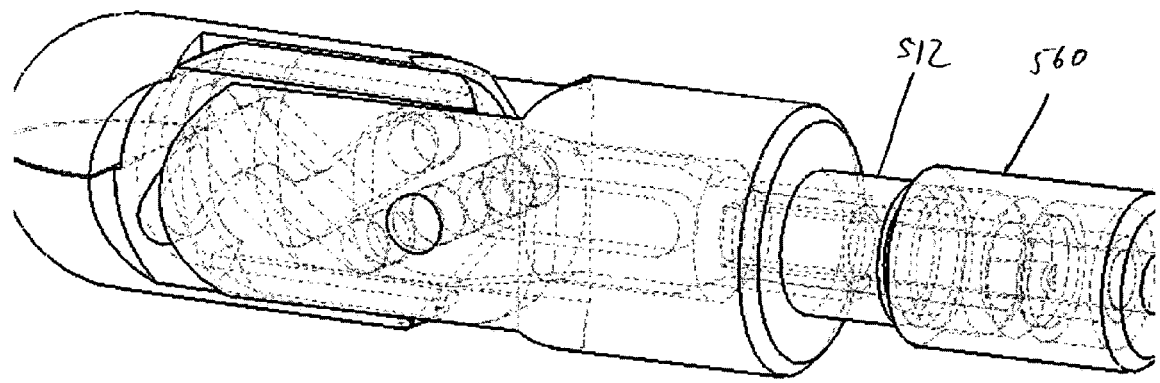
FIG. 40 is a fragmentary, enlarged, partially broken away hidden line perspective view of the end effector of FIG. 39 and with the fracturing portion in a second fracturing position.
Figure 41:
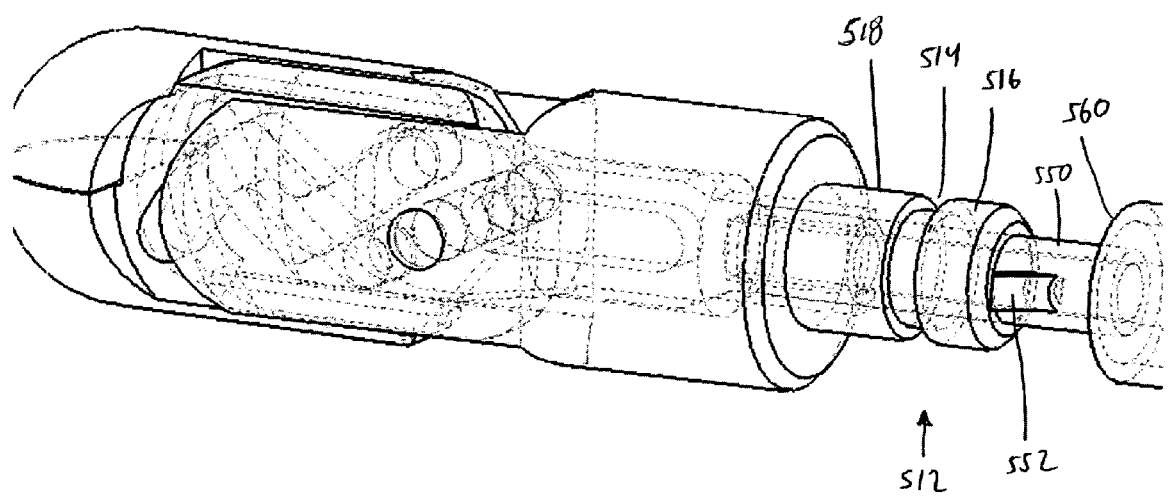
FIG. 41 is a fragmentary, enlarged, partially broken away hidden line perspective view of the end effector of FIG. 40 and with the fracturing portion in a third fracturing position and a spring catch in a catching position.

Once the distal edge of the spring catch 552 passes the proximal-most exterior surface of the barb 512, as shown in FIGS. 40 to 41, the spring catch 552 springs outward to prevent any later distal movement of the fracture piston 550 into the clevis 510.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

We claim:

1. A medical guidewire system for guiding thereon a medical implement, comprising:
a surgical end effector for carrying out a medical procedure when actuated;
an actuation guidewire having a distal end connected to said end effector;
a control assembly having:
a handle;

a hollow shaft receiving therein at least a portion of said actuation guidewire, said shaft having:
  a proximal end connected to said handle; and
  a distal end removably connected to said end effector;
an actuator movably connected to said handle and operatively connected to said actuation guidewire to actuate said end effector by said actuation guidewire through said shaft when said actuator is actuated, wherein said actuator, when actuated, moves said actuation guidewire within an actuation range; and
a proximally directed force imparter movably connected to said handle and operatively connected to a portion of said actuation guidewire to disconnect said actuation guidewire from said handle when said proximally directed force imparter is actuated and, thereby, permit removal of said control assembly from said end effector and said actuation guidewire and, when said control assembly is removed, said end effector and said actuation guidewire forming a surgical guidewire for guiding thereon the medical implement, wherein said proximally directed force imparter, when actuated, moves said actuation guidewire outside said actuation range to disconnect said actuation guidewire from said control assembly.

2. The system according to claim 1, wherein said end effector and said shaft are sized to pass through at least one of:
  a working channel of an endoscope;
  a lumen of a catheter sheath introducer; and
  a lumen of a trocar.

3. The system according to claim 1, wherein said end effector is a dissection device.

4. The system according to claim 3, wherein said dissection device is shaped to traverse a Chronic Total Occlusion.

5. The system according to claim 1, wherein said shaft has:
  an inner sheath surrounding a portion of said actuation guidewire;
  a coil surrounding said inner sheath;
  a sheath casing surrounding said coil; and
  a strain relief disposed at a junction of said handle and said coil and said sheath casing and surrounding said sheath casing.

6. The system according to claim 5, wherein said coil is of stainless steel.

7. The system according to claim 5, wherein said sheath casing is of a material selected from at least one of the group consisting of a fluoropolymer and a polyolefin.

8. The system according to claim 5, wherein said strain relief is of a heat-shrinkable material.

9. The system according to claim 8, wherein said heat-shrinkable material is selected from at least one of the group consisting of polyurethane and polyolefin.

10. The system according to claim 1, wherein:
  said actuation guidewire moves inside said handle when said first actuator is actuated; and
  said actuator is a trigger assembly having:
    an actuation coupler connected to said actuation guidewire and movably disposed inside said handle to move in a corresponding manner with said actuation guidewire;
    a trigger body pivotally connected to said handle; and
    a trigger link having a first end pivotally connected to said trigger body and a second end pivotally connected to said actuation coupler, said trigger link moving said actuation coupler and, thereby, said actuation guidewire, when said trigger is actuated.

11. The system according to claim 10, wherein said proximally directed force imparter is connected to at least one of said actuation coupler and said actuation guidewire.

12. The system according to claim 11, wherein:
  said actuation coupler moves in said actuation range when said trigger body is actuated; and
  said proximally directed force imparter is connected to said actuation coupler and moves said actuation coupler outside said actuation range when actuated.

13. The system according to claim 1, wherein said proximally directed force imparter, when actuated, moves at least a portion of said actuation guidewire within said handle longitudinally further away from said end effector.

14. The system according to claim 1, wherein said proximally directed force imparter is a lever that, when pivoted, moves said actuation guidewire outside said actuation range.

15. The system according to claim 1, wherein said proximally directed force imparter is a screw that, when unscrewed, moves said actuation guidewire outside said actuation range.

16. A medical guidewire system for guiding thereon a medical implement, comprising:
  a surgical end effector for carrying out a medical procedure when actuated;
  an actuation guidewire having a distal end connected to said end effector;
  a control assembly having:
    a handle having a boss; and
    a hollow shaft receiving therein at least a portion of said actuation guidewire, said shaft having:
      a proximal end connected to said handle; and
      a distal end removably connected to said end effector;
    an actuator movably connected to said handle and operatively connected to said actuation guidewire to actuate said end effector by said actuation guidewire through said shaft when said actuator is actuated; and
    a proximally directed force imparter movably connected to said handle and operatively connected to a portion of said actuation guidewire to disconnect said actuation guidewire from said handle when said proximally directed force imparter is actuated and, thereby, permit removal of said control assembly from said end effector and said actuation guidewire and, when said control assembly is removed, said end effector and said actuation guidewire forming a surgical guidewire for guiding thereon the medical implement,
    wherein said distal end of said actuation guidewire is a first end running from said end effector, through said shaft in a proximal direction, around said boss, back through said shaft in a distal direction, and terminating at a removable connection on said end effector.

17. The system according to claim 16, wherein actuation of said actuator moves said actuation guidewire in an actuation range insufficient to break said removable connection and actuation of said proximally directed force imparter moves said actuation guidewire outside said actuation range sufficient to break said removable connection.

18. A medical guidewire system for guiding thereon a medical implement, comprising:
  a surgical end effector for carrying out a medical procedure when actuated;
  an actuation guidewire having a distal end connected to said end effector;
  a control assembly having:
    a handle;
    a hollow shaft receiving therein at least a portion of said actuation guidewire, said shaft having:

a proximal end connected to said handle; and a distal end removably connected to said end effector;

an actuator movably connected to said handle and operatively connected to said actuation guidewire to actuate said end effector by said actuation guidewire through said shaft when said actuator is actuated; and a proximally directed force imparter movably connected to said handle and operatively connected to a portion of said actuation guidewire to disconnect said actuation guidewire from said handle when said proximally directed force imparter is actuated and, thereby, permit removal of said control assembly from said end effector and said actuation guidewire and, when said control assembly is removed, said end effector and said actuation guidewire forming a surgical guidewire for guiding thereon the medical implement, wherein:

said end effector has a frangible portion removably connecting said shaft to said end effector;

said actuator, when actuated, moves said actuation guidewire within an actuation range in which said frangible portion remains connected to said end effector; and said proximally directed force imparter, when actuated, moves said actuation guidewire outside said actuation range to disconnect said actuation guidewire from said control assembly and disconnect said frangible portion from said end effector, thereby disconnecting said shaft from said end effector.

19. The system according to claim 18, wherein said frangible portion is fixed to said shaft when said proximally directed force imparter is actuated and said frangible tube is disconnected from said end effector.

20. The system according to claim 19, wherein:

said shaft has:

a coil surrounding at least a portion of said actuation guidewire; and a sheath casing surrounding said coil;

said end effector has a clevis with a proximal end; and said frangible portion is a fracture tube removably connected to said proximal end of said clevis and extending in a proximal direction therefrom into at least a portion of said coil and said sheath casing.

* * * * *